(12) United States Patent
Brown

(10) Patent No.: US 10,736,778 B2
(45) Date of Patent: Aug. 11, 2020

(54) GLAUCOMA TREATMENT DEVICES AND METHODS

(71) Applicant: MicroOptx Inc., Maple Grove, MN (US)

(72) Inventor: J. David Brown, St. Paul, MN (US)

(73) Assignee: MicroOptx Inc., Maple Grove, MN (US)

( * ) Notice: Subject to any disclaimer, the term of this patent is extended or adjusted under 35 U.S.C. 154(b) by 587 days.

(21) Appl. No.: 15/540,904

(22) PCT Filed: Dec. 30, 2015

(86) PCT No.: PCT/US2015/068017
§ 371 (c)(1),
(2) Date: Jun. 29, 2017

(87) PCT Pub. No.: WO2016/109639
PCT Pub. Date: Jul. 7, 2016

(65) Prior Publication Data
US 2017/0367888 A1 Dec. 28, 2017

Related U.S. Application Data

(60) Provisional application No. 62/235,113, filed on Sep. 30, 2015, provisional application No. 62/098,609, filed on Dec. 31, 2014.

(51) Int. Cl.
A61F 9/007 (2006.01)
A61L 27/18 (2006.01)
A61L 27/28 (2006.01)

(52) U.S. Cl.
CPC .......... A61F 9/00781 (2013.01); A61L 27/18 (2013.01); A61L 27/28 (2013.01);
(Continued)

(58) Field of Classification Search
CPC .......... A61F 9/00781; A61F 2220/0016; A61F 2220/0033; A61F 2250/006; A61L 27/18; A61L 27/28; A61M 27/002
See application file for complete search history.

(56) References Cited

U.S. PATENT DOCUMENTS 3,159,161 A 12/1964 Ness
3,788,327 A 1/1974 Donowitz
(Continued)

FOREIGN PATENT DOCUMENTS

CN 1285724 2/2001
CN 1189780 2/2005
(Continued)

OTHER PUBLICATIONS

Japanese Office Action in Japanese Application No. 2017-535810, dated Jul. 8, 2019, 47 pages.
(Continued)

Primary Examiner — Philip R Wiest
(74) Attorney, Agent, or Firm — Fish & Richardson P.C.

(57) ABSTRACT

Devices can be implanted in an eye to treat glaucoma. The devices described herein include a body defining a lumen and having first and second ends and external and lumenal surfaces. The body has a length sufficient to provide fluid communication between the anterior chamber and tear film of the eye through the lumen when the device is implanted in the sclera. By the strategic selection of particular materials of construction, and/or by controlling the configuration and size of the lumen, in some embodiments, the device is a filterless construct. In some embodiments, a filter is included. The glaucoma treatment devices as provided herein are designed to prevent bacterial ingress and to provide the required level of outflow resistance to achieve a desired intraocular pressure. Methods of treating glaucoma (Continued)

wherein the device is implanted in the sclera of an afflicted eye are also described.

14 Claims, 21 Drawing Sheets

(52) U.S. Cl.
CPC ................ A61F 2220/0016 (2013.01); A61F 2220/0033 (2013.01); A61F 2250/006 (2013.01)

(56) References Cited

U.S. PATENT DOCUMENTS

| | | | |
|---|---|---|---|
| 4,402,681 A | 9/1983 | Haas et al. |
| 4,457,757 A | 7/1984 | Molteno |
| 4,521,210 A | 6/1985 | Wong |
| 4,554,918 A | 11/1985 | White |
| 4,604,087 A | 8/1986 | Joseph |
| 4,634,418 A | 1/1987 | Binder |
| 4,655,745 A | 4/1987 | Corbett |
| 4,722,724 A | 2/1988 | Schocket |
| 4,729,761 A | 3/1988 | White |
| 4,750,901 A | 6/1988 | Molteno |
| 4,758,237 A | 7/1988 | Sacks |
| 4,787,885 A | 11/1988 | Binder |
| 4,826,478 A | 5/1989 | Schocket |
| 4,836,931 A | 6/1989 | Spearman et al. |
| 4,886,488 A | 12/1989 | White |
| 4,936,825 A | 6/1990 | Ungerleider |
| 4,946,436 A | 8/1990 | Smith |
| 4,968,296 A | 11/1990 | Ritch et al. |
| 5,041,081 A | 8/1991 | Odrich |
| 5,071,408 A | 12/1991 | Ahmed |
| 5,073,163 A | 12/1991 | Lippman |
| 5,092,837 A | 3/1992 | Ritch et al. |
| 5,127,901 A | 7/1992 | Odrich |
| 5,171,213 A | 12/1992 | Price, Jr. |
| 5,178,604 A | 1/1993 | Baerveldt et al. |
| 5,300,020 A | 4/1994 | L'Esperance, Jr. |
| 5,342,370 A | 8/1994 | Simon et al. |
| 5,344,454 A | 9/1994 | Clarke et al. |
| 5,346,464 A | 9/1994 | Camras |
| 5,360,399 A | 11/1994 | Stegmann |
| 5,370,607 A | 12/1994 | Memmen |
| 5,372,577 A | 12/1994 | Ungerleider |
| 5,380,328 A | 1/1995 | Morgan |
| 5,397,300 A | 3/1995 | Baerveldt et al. |
| 5,417,855 A | 5/1995 | Gershenson |
| 5,433,701 A | 6/1995 | Rubinstein |
| 5,454,796 A | 10/1995 | Krupin |
| 5,476,445 A | 12/1995 | Baerveldt et al. |
| 5,489,300 A | 2/1996 | Capecchi et al. |
| 5,496,372 A | 3/1996 | Hamamoto et al. |
| 5,558,629 A | 9/1996 | Baerveldt et al. |
| 5,558,630 A | 9/1996 | Fisher |
| 5,573,544 A | 11/1996 | Simon et al. |
| RE35,390 E | 12/1996 | Smith |
| 5,626,558 A | 5/1997 | Suson |
| 5,626,559 A | 5/1997 | Solomon |
| 5,651,782 A | 7/1997 | Simon et al. |
| 5,651,900 A | 7/1997 | Keller et al. |
| 5,676,679 A | 10/1997 | Simon et al. |
| 5,695,989 A | 12/1997 | Kalamasz |
| 5,702,414 A | 12/1997 | Richter et al. |
| 5,704,907 A | 1/1998 | Nordquist et al. |
| 5,725,493 A | 3/1998 | Avery et al. |
| 5,743,868 A | 4/1998 | Brown et al. |
| 5,752,928 A | 5/1998 | de Roulhac et al. |
| 5,753,014 A | 5/1998 | Van Rijn |
| 5,785,674 A | 7/1998 | Mateen |
| 5,798,042 A | 8/1998 | Chu et al. |
| 5,807,302 A | 9/1998 | Wandel |
| 5,807,406 A | 9/1998 | Brauker et al. |
| 5,868,697 A | 2/1999 | Richter et al. |
| 5,879,319 A | 3/1999 | Pynson et al. |
| 5,882,327 A | 3/1999 | Jacob |
| 5,891,084 A | 4/1999 | Lee |
| 5,893,837 A | 4/1999 | Eagles et al. |
| 5,893,974 A | 4/1999 | Keller et al. |
| 5,919,364 A | 7/1999 | Lebouitz et al. |
| 5,922,210 A | 7/1999 | Brody et al. |
| 5,968,058 A | 10/1999 | Richter et al. |
| 6,007,511 A | 12/1999 | Prywes |
| 6,044,981 A | 4/2000 | Chu et al. |
| 6,050,970 A | 4/2000 | Baerveldt |
| 6,073,163 A | 6/2000 | Clark et al. |
| 6,077,299 A | 6/2000 | Adelberg et al. |
| 6,077,422 A | 6/2000 | Ryles |
| 6,102,045 A | 8/2000 | Nordquist et al. |
| 6,139,757 A | 10/2000 | Ohmura et al. |
| 6,142,969 A | 11/2000 | Nigam |
| 6,168,575 B1 | 1/2001 | Soltanpour |
| 6,186,974 B1 | 2/2001 | Allan et al. |
| 6,203,513 B1 | 3/2001 | Yaron et al. |
| 6,277,855 B1 | 8/2001 | Yerxa |
| 6,280,449 B1 | 8/2001 | Blake |
| 6,322,895 B1 | 11/2001 | Canham |
| 6,387,379 B1 | 5/2002 | Goldberg et al. |
| 6,468,283 B1 | 10/2002 | Richter et al. |
| 6,510,600 B2 | 1/2003 | Yaron et al. |
| 6,515,346 B1 | 2/2003 | Kemeny |
| 6,544,208 B2 | 4/2003 | Ethier et al. |
| 6,595,945 B2 | 7/2003 | Brown |
| 6,598,750 B2 | 7/2003 | Tai et al. |
| 6,613,241 B1 | 9/2003 | Scherer et al. |
| 6,622,872 B1 | 9/2003 | Tai et al. |
| 6,638,239 B1 | 10/2003 | Bergheim et al. |
| 6,666,841 B2 | 12/2003 | Gharib et al. |
| D490,152 S | 5/2004 | Myall et al. |
| 6,736,791 B1 | 5/2004 | Tu et al. |
| 6,780,164 B2 | 8/2004 | Bergheim et al. |
| 6,881,198 B2 | 4/2005 | Brown |
| 6,955,656 B2 | 10/2005 | Bergheim et al. |
| 6,981,958 B1 | 1/2006 | Gharib et al. |
| 7,054,011 B2 | 5/2006 | Zhu et al. |
| 7,094,225 B2 | 8/2006 | Tu et al. |
| 7,135,009 B2 | 11/2006 | Tu et al. |
| 7,163,543 B2 | 1/2007 | Smedley et al. |
| 7,172,076 B2 | 2/2007 | Kneezel |
| 7,192,412 B1 | 3/2007 | Zhou et al. |
| 7,226,540 B2 | 6/2007 | Rodgers et al. |
| 7,364,564 B2 | 4/2008 | Sniegowski et al. |
| 7,384,550 B2 | 6/2008 | Rodgers et al. |
| 7,641,627 B2 | 1/2010 | Camras et al. |
| 7,708,711 B2 | 5/2010 | Tu et al. |
| 7,862,531 B2 | 1/2011 | Yaron et al. |
| 2001/0000527 A1 | 4/2001 | Yaron et al. |
| 2002/0143284 A1 | 10/2002 | Tu et al. |
| 2002/0169468 A1* | 11/2002 | Brown ............... A61F 9/00781 606/161 |
| 2003/0078487 A1 | 4/2003 | Jeffries et al. |
| 2003/0080060 A1 | 5/2003 | Gulvin |
| 2003/0212383 A1 | 11/2003 | Cote et al. |
| 2004/0050392 A1 | 3/2004 | Tu et al. |
| 2004/0127843 A1 | 7/2004 | Tu et al. |
| 2004/0260227 A1 | 12/2004 | Lisk, Jr. et al. |
| 2005/0032691 A1 | 2/2005 | Wax et al. |
| 2005/0033265 A1 | 2/2005 | Engel et al. |
| 2005/0119737 A1 | 6/2005 | Bene et al. |
| 2005/0137146 A1 | 6/2005 | Landers et al. |
| 2005/0194303 A1 | 9/2005 | Sniegowski et al. |
| 2005/0197653 A1 | 9/2005 | Sniegowski et al. |
| 2006/0025849 A1* | 2/2006 | Kaplan ............... A61F 2/915 623/1.15 |
| 2006/0036207 A1 | 2/2006 | Koonmen et al. |
| 2006/0079828 A1 | 4/2006 | Brown |
| 2006/0116626 A1 | 6/2006 | Smedley et al. |
| 2006/0148926 A1 | 7/2006 | Bide et al. |
| 2006/0235367 A1 | 10/2006 | Takashima et al. |
| 2006/0241749 A1 | 10/2006 | Tu et al. |
| 2006/0276739 A1* | 12/2006 | Brown ............... A61F 9/00781 604/8 |
| 2007/0233240 A1 | 10/2007 | Frank et al. |

(56) References Cited

U.S. PATENT DOCUMENTS

| | | | |
|---|---|---|---|
| 2008/0015689 | A1 | 1/2008 | Esch et al. |
| 2008/0161741 | A1 | 7/2008 | Bene et al. |
| 2009/0117166 | A1 | 5/2009 | Myung et al. |
| 2010/0056977 | A1 | 3/2010 | Wandel |
| 2010/0189765 | A1 | 7/2010 | Erickson et al. |
| 2013/0267887 | A1* | 10/2013 | Kahook ............... B29C 53/02 604/9 |
| 2014/0371651 | A1 | 12/2014 | Pinchuk |
| 2015/0005689 | A1* | 1/2015 | Horvath ............ A61F 9/00781 604/8 |
| 2015/0094641 | A1* | 4/2015 | Park .................. A61F 9/00781 604/8 |
| 2017/0367888 | A1 | 12/2017 | Brown |
| 2018/0280195 | A1 | 10/2018 | Brown |

FOREIGN PATENT DOCUMENTS

| | | |
|---|---|---|
| CN | 101001589 | 7/2007 |
| CN | 101522132 | 9/2009 |
| CN | 103476371 | 12/2013 |
| CN | 104168863 | 11/2014 |
| EP | 2896386 | 7/2015 |
| JP | H11-505159 | 5/1999 |
| JP | 2000-237302 | 9/2000 |
| JP | 2008-500878 | 1/2008 |
| JP | 2009-508584 | 3/2009 |
| WO | WO 1996/36377 | 11/1996 |
| WO | WO 1999/26567 | 6/1999 |
| WO | WO 2000/062760 | 10/2000 |
| WO | WO 2001/50943 | 7/2001 |
| WO | WO 2002/36052 | 5/2002 |
| WO | WO 2005/081967 | 9/2005 |
| WO | WO 2005/081968 | 9/2005 |
| WO | WO 2005/117780 | 12/2005 |
| WO | WO 2007/035356 | 3/2007 |
| WO | WO 2011/075481 | 6/2011 |
| WO | WO 2011/089605 | 7/2011 |
| WO | WO 2012/040380 | 3/2012 |
| WO | WO 2013/114214 | 8/2013 |

OTHER PUBLICATIONS

"Ex-PressTM Miniature Glaucoma Implant," Optonol Ltd. Brochure, 7 pages.

"Polycrystalline silicon," Wikipedia [online], Mar. 7, 2008 [retrieved on Apr. 6, 2008]. Retrieved from the Internet: URL: <http://en.wikipedia.org/wiki/Polysilicon>, 4 pages.

Alexeev et al., "High Ionic Strength Glucose-Sensing Photonic Crystal," *Anal Chem.*, 75(10):2316-2323, May 2003.

Alexeev et al., "Photonic crystal glucose-sensing material for non-invasive monitoring of glucose in tear fluid," *Clin Chem.*, 50(12):2353-2360, Dec. 2004.

Allan, "Closer to nature: new biomaterials and tissue engineering in ophthalmology," *Br J Ophthalmol.*, 83(11):1235-1240, 1999.

Alward, "Introduction," "Optic Nerve Head Anatomy and Physiology," "Aqueous System Anatomy and Physiology," and "Aqueous Drainage Devices," *Glaucoma—The Requisites in Ophthalmology.*, pp. xi-xii, 3-16, and 228-233.

Belkin et al., "Evaluation of the Ex-PressTM Miniature Glaucoma Implant in Glaucoma Patients," *The 6th Congress of the European Glaucoma Society Millennium Meeting*, London, 2000.

Brody et al., "A Planar Microfabricated Fluid Filter," University of Washington (1996).

Brown, "A New Device for the Treatment of Glaucoma," Powerpoint presentation.

Chen et al., "FDA Report: SmartFlow Glaucoma Stent," Coursework Submission, 2003, Retrieved from the Internet: URL <http://pergatory.mit.edu/pwilloughby/docs/glaucoma_fda_report.pdf>, 10 pages.

Chen et al., "Final Report: SmartFlow Glaucoma Stent," Coursework Submission, 2003, Retrieved from the Internet: URL <http://pergatory.mit.edu/pwilloughby/docs/glaucoma_final_report.pdf>, 19 pages.

Extended European Search Report in Application No. EP15876235.1, dated Aug. 21, 2018, 9 pages.

Hanein et al., "Micromachining of non-fouling coatings for bio-MEMS Applications," *Sensors and Actuators B.*, 81:49-54, 2001.

Howorth, "Feasibility Study for a Micromachined Glaucoma Drainage Device," Masters Thesis, 2002, Cranfield University, 152 pages.

International Preliminary Report on Patentability in Application No. PCT/US2015/068017, dated Jul. 13, 2017, 8 pages.

International Search Report and Written Opinion in Application No. PCT/US2015/068017, dated May 3, 2016, 11 pages.

Invitation to Pay Additional Fees in Application No. PCT/US2015/068017, dated Feb. 19, 2016, 2 pages.

Lim et al., "Cell and protein adhesion studies in glaucoma drainage device development," *Br. J. Ophthalmol.*, 83:1168-1171, 1999.

Millipore product specifications. "Omnipore Memberane Filter" http://www.millipore.com/catalogue/item/gwp04700 Accessed 156 Nov. 2012.

Pan et al., "A Microfluid Test-Bed with Nanopore Membranes for In-Vitro Simulation of Flow Characteristics of Glaucoma Drainage Devices," presented at Houston BME Conference, Oct. 26, 2002, 2 pages.

Sim and Kim, "A Study on the Passive Microvalve Applicable to Drainage Device for Glaucoma," *J. Semiconductor Technology and Science.*, 2(4):253-258, 2002.

Spiegel et al., "Schlemm's Canal Implant: A New Method to Lower Intraocular Pressure in Patients with POAG?" *Ophthalmic Surgery and Lasers.*, 30(6):492-494, 1999.

Vaughan and Asbury, General Ophthalmology, 8th edition, Langue Medical Publications, pp. 1-8.

Yang et al., "Micromachined Membrane Particle Filters," IEEE 11th International Workshop on Micro Electro Mechanical Systems, Jan. 25-29, 1998, Heidelberg, Germany, 6 pages.

Yang et al., "Micromachined membrane particle filters," *Sensors and Actuators A.*, 73:184-191, 1999.

Chinese Office Action in Chinese Application No. 201580077239.1, dated Jun. 6, 2019, 29 pages.

Extended European Search Report in Application No. 16852726.5, dated May 24, 2019, 181 pages.

International Search Report in International Application No. PCT/US2016/054828 dated Dec. 31, 2016, 2 pages.

Second Chinese Office Action in Chinese Application No. 201580077239.1, dated Dec. 30, 2019, 27 pages.

\* cited by examiner

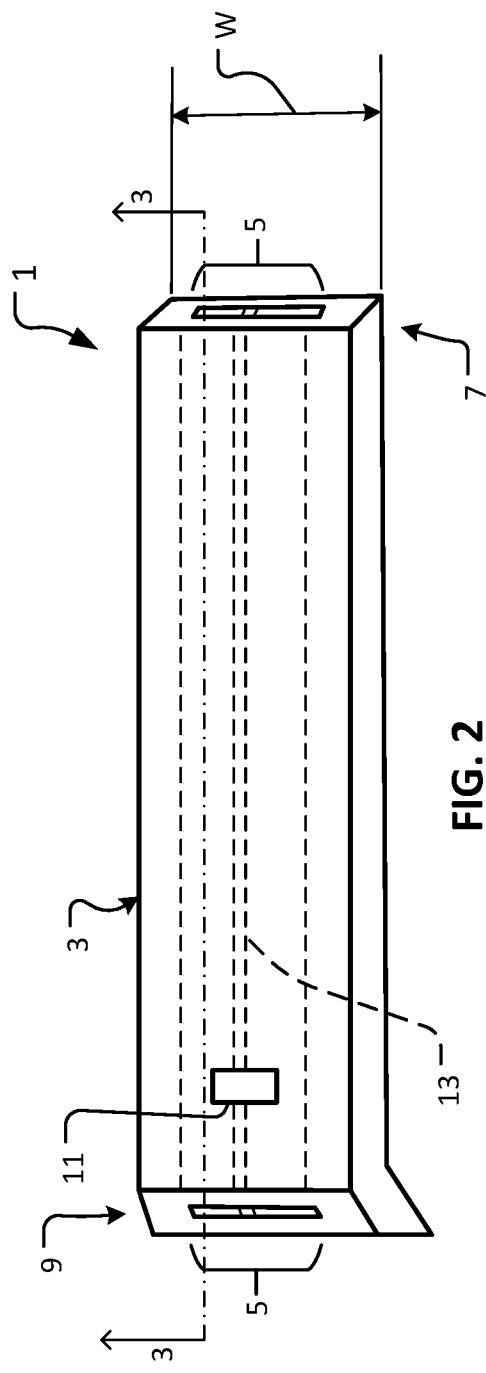
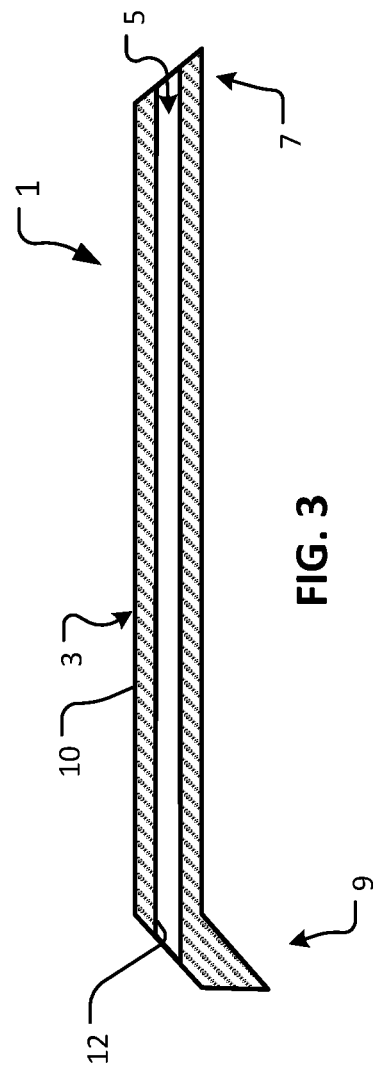
FIG. 2
FIG. 3

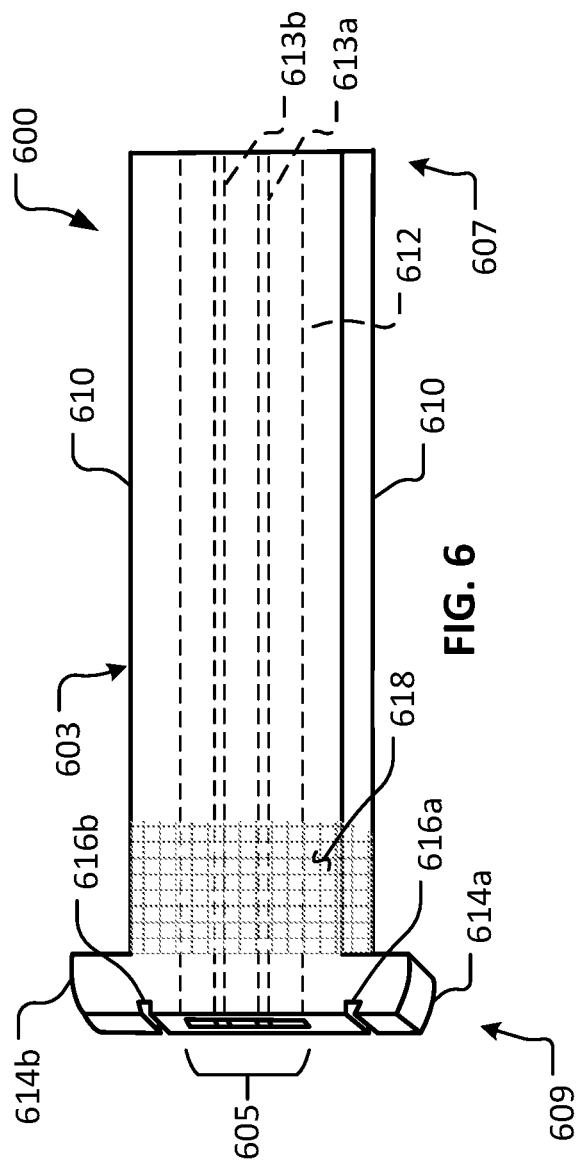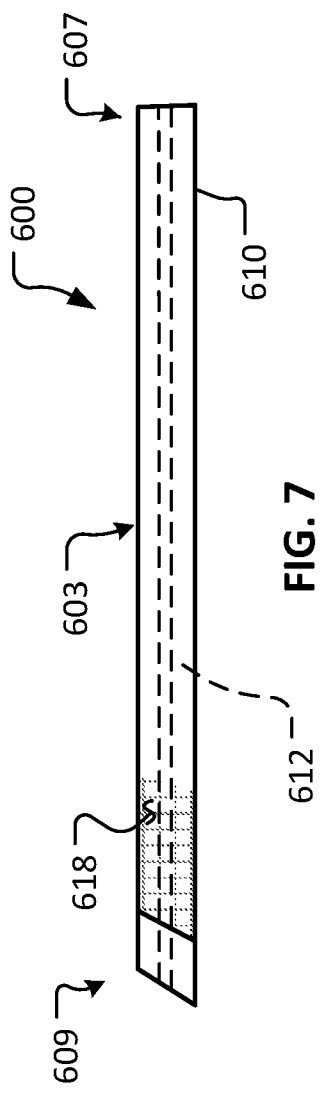

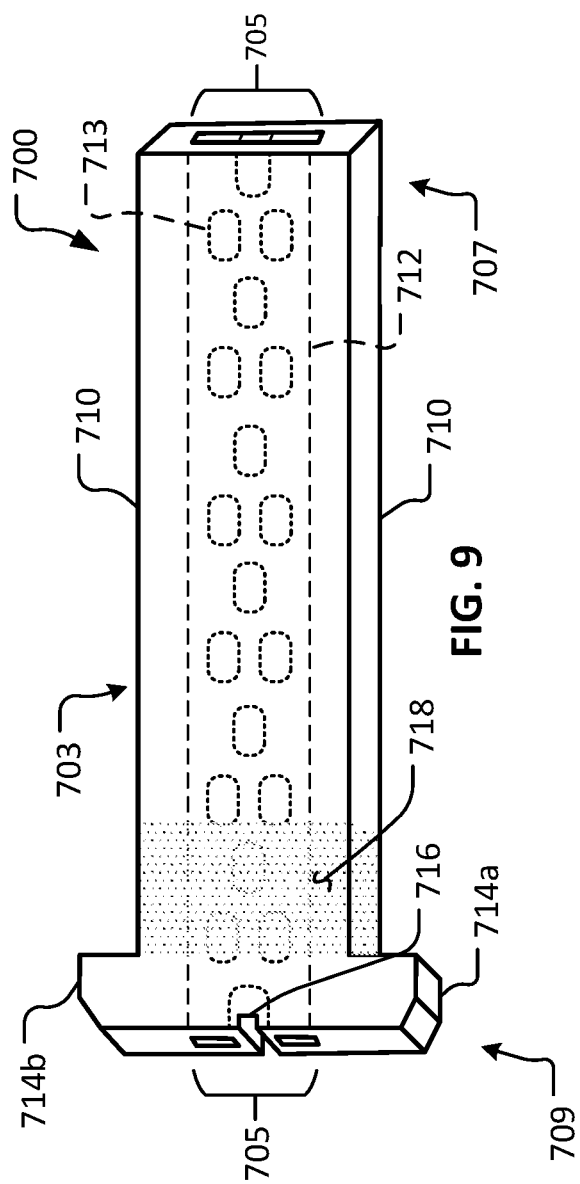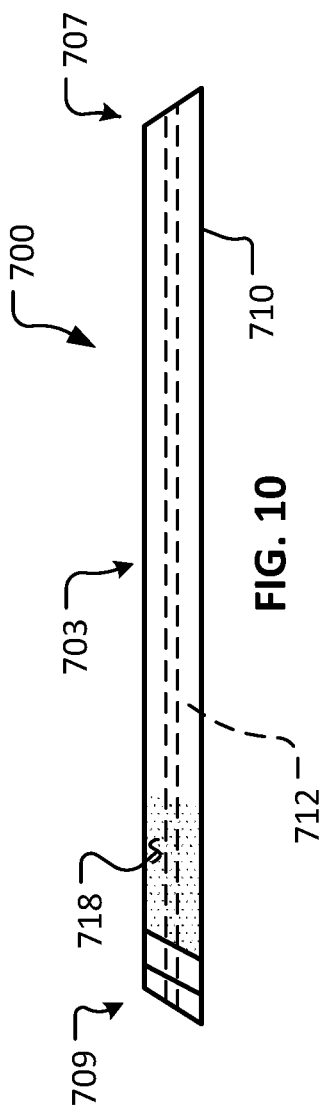

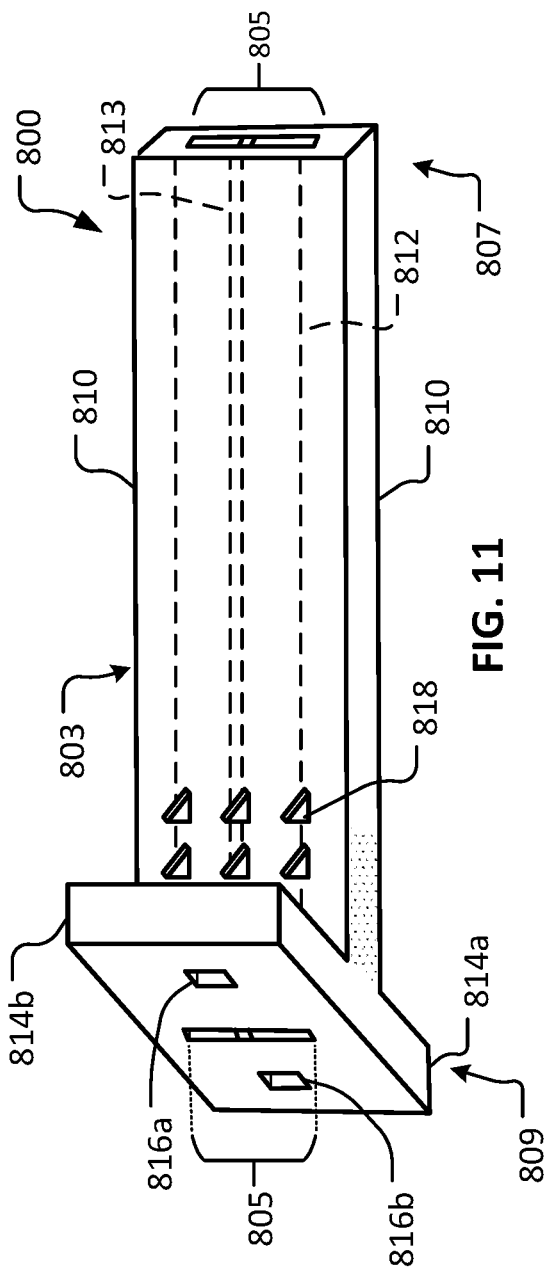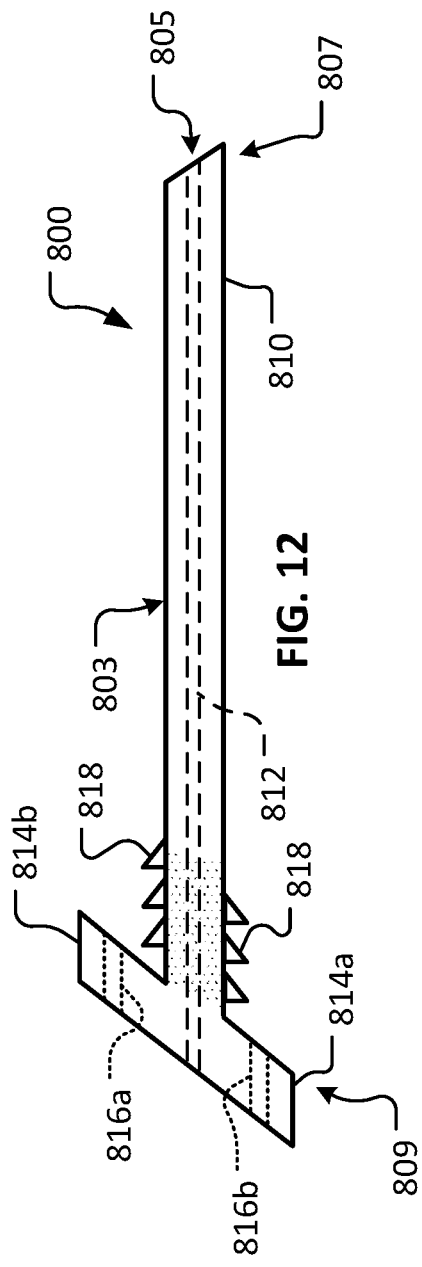

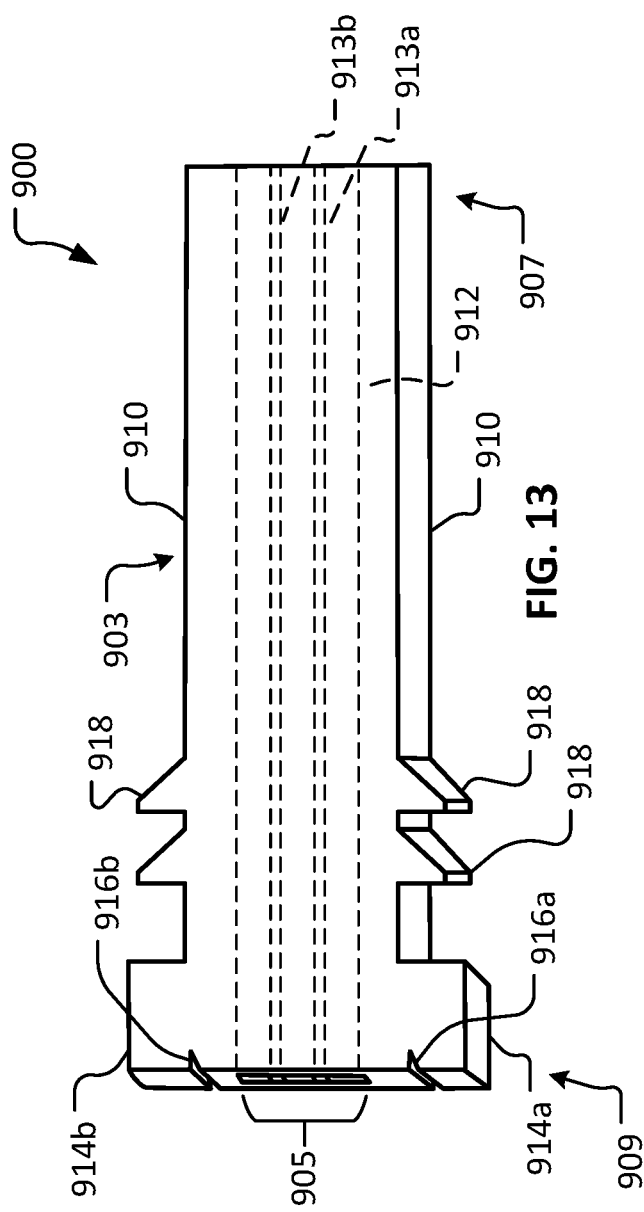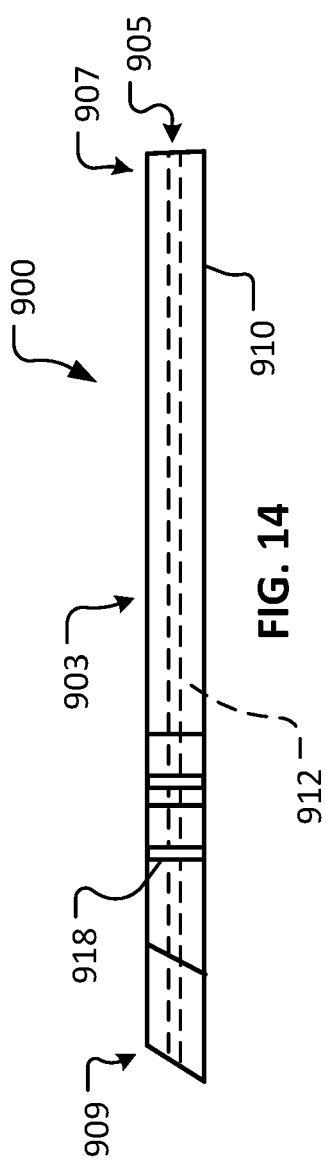

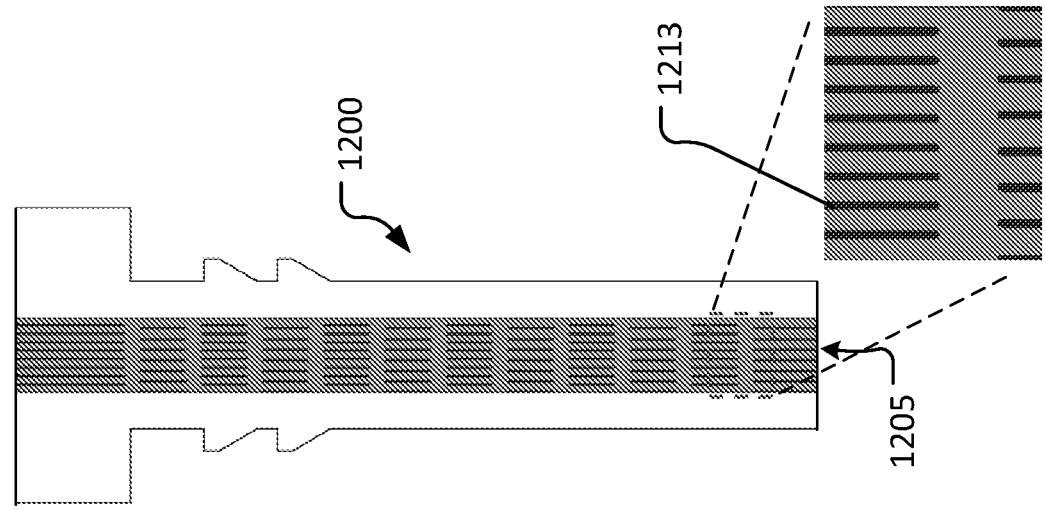
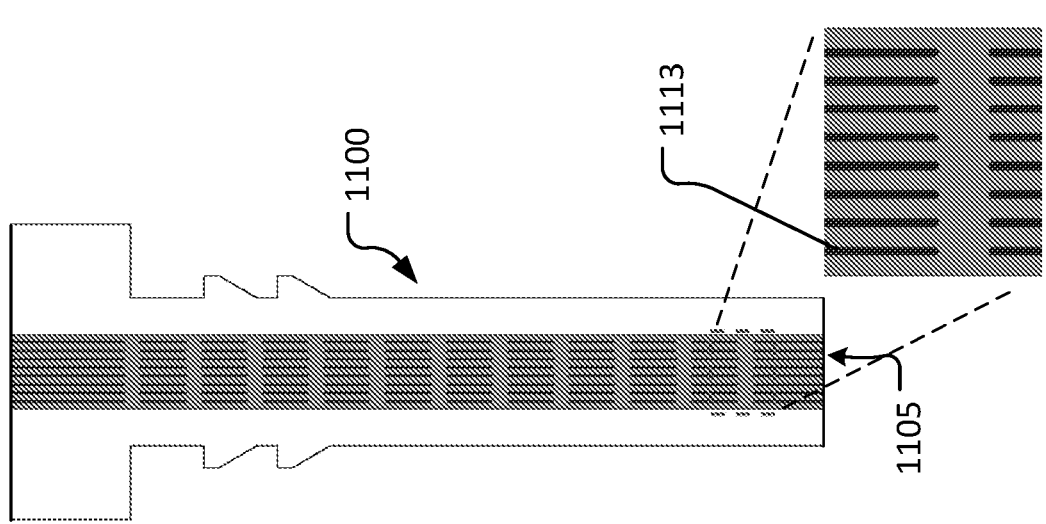
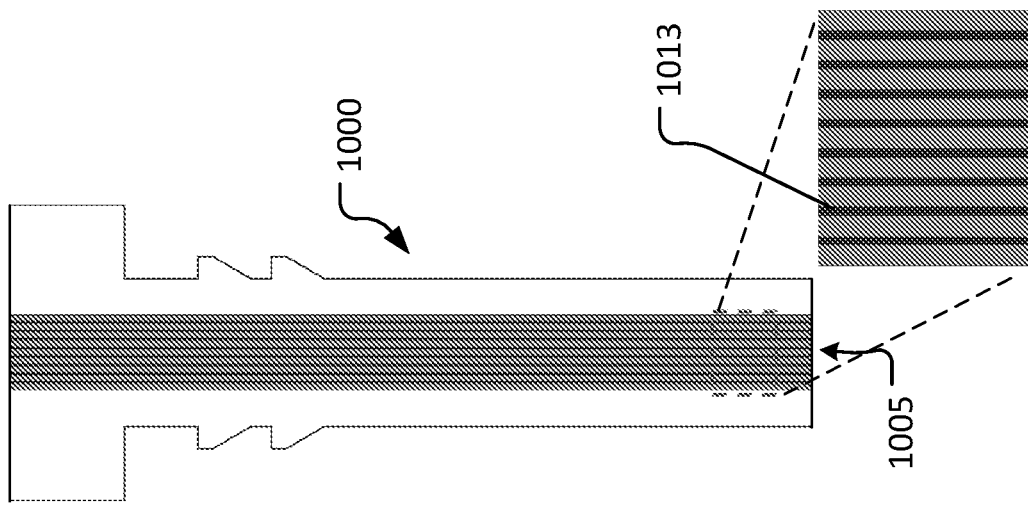

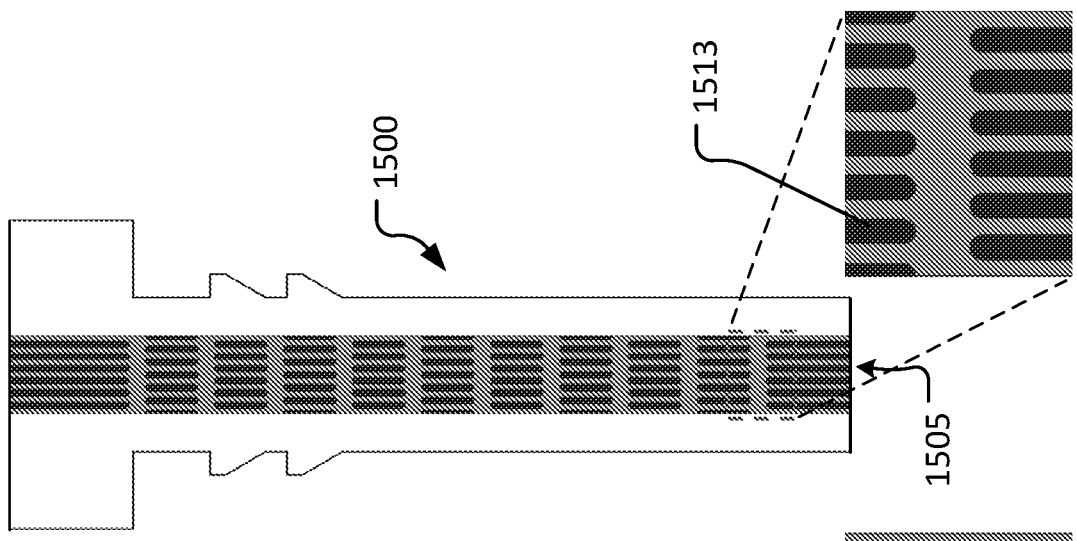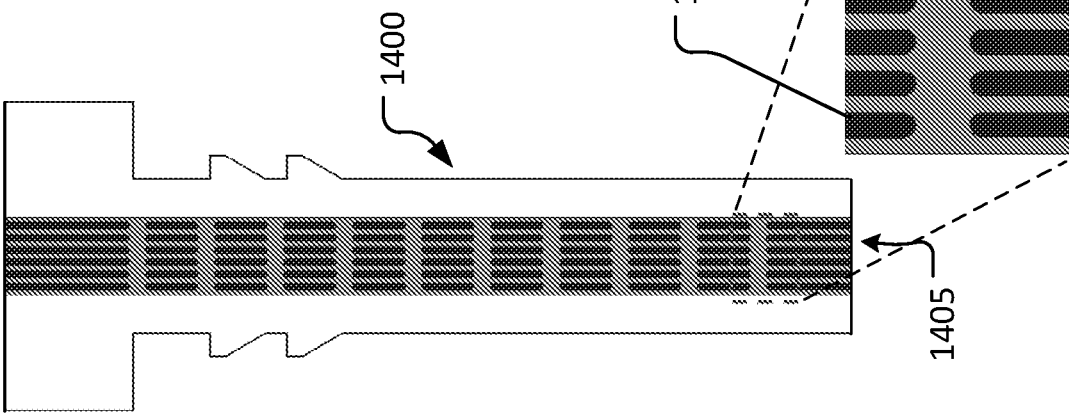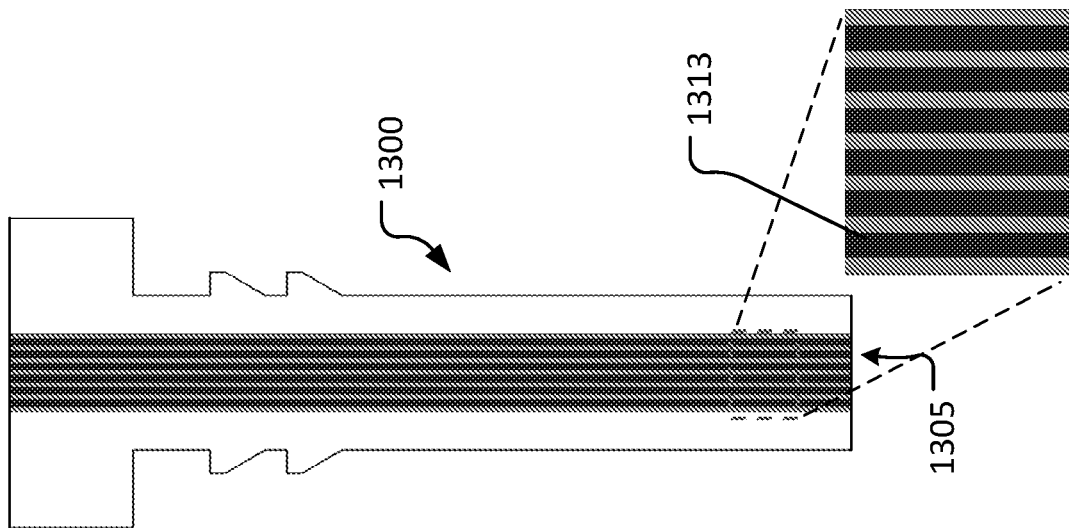

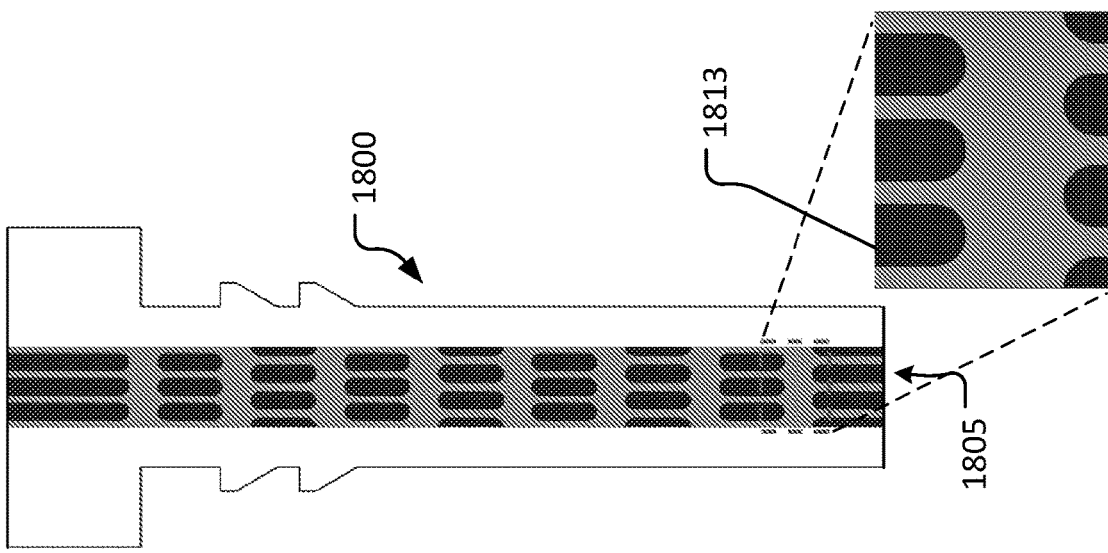
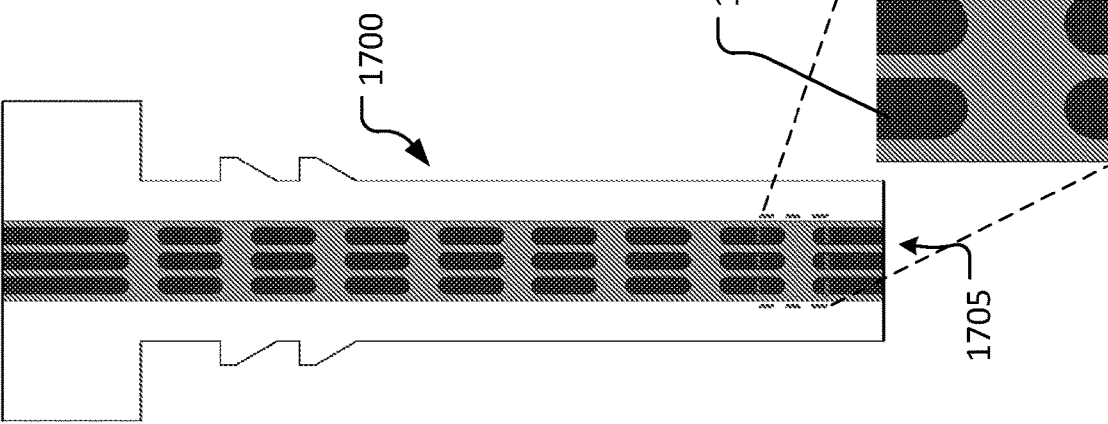
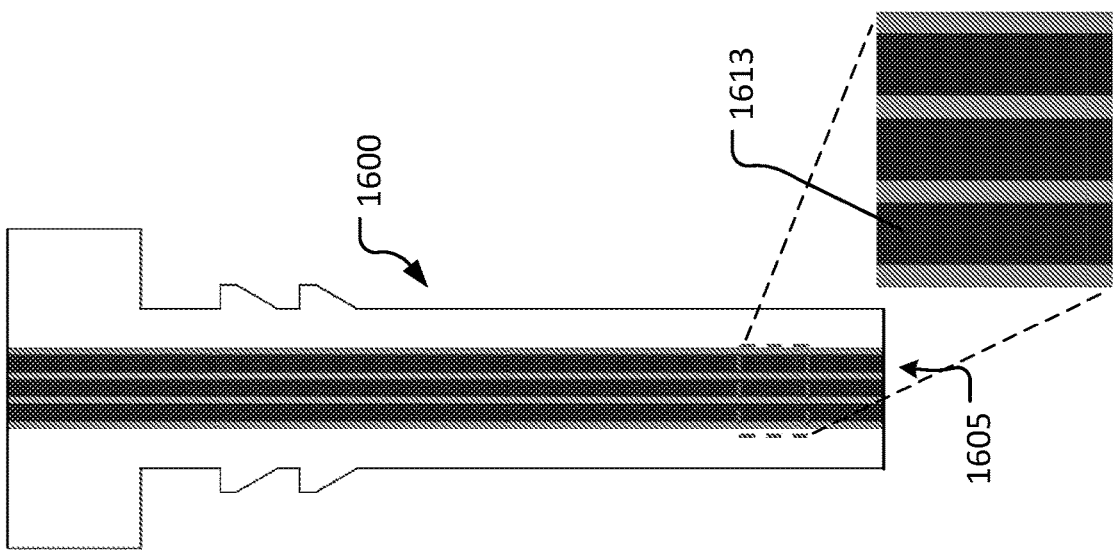

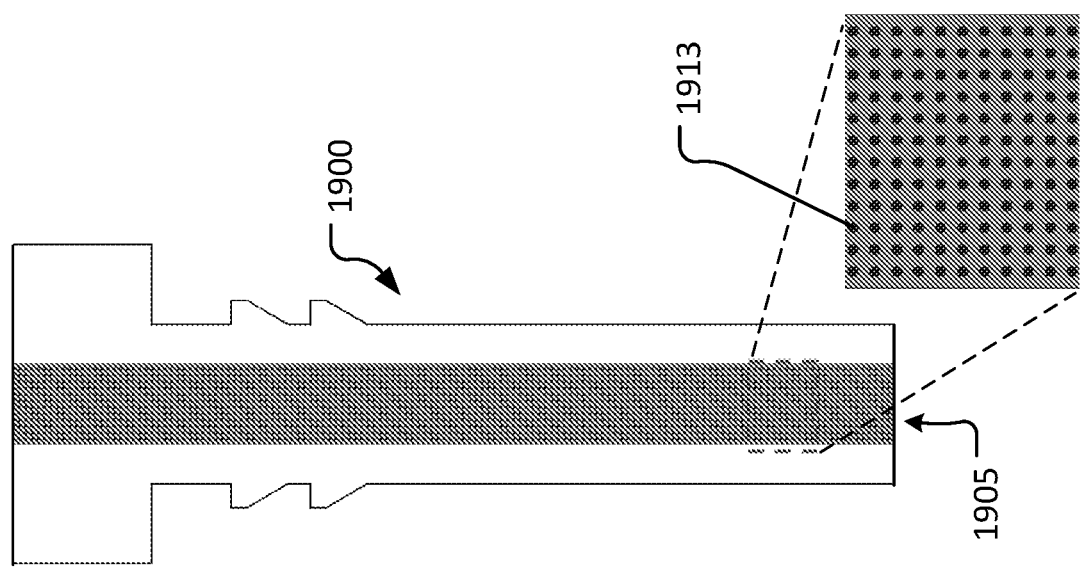
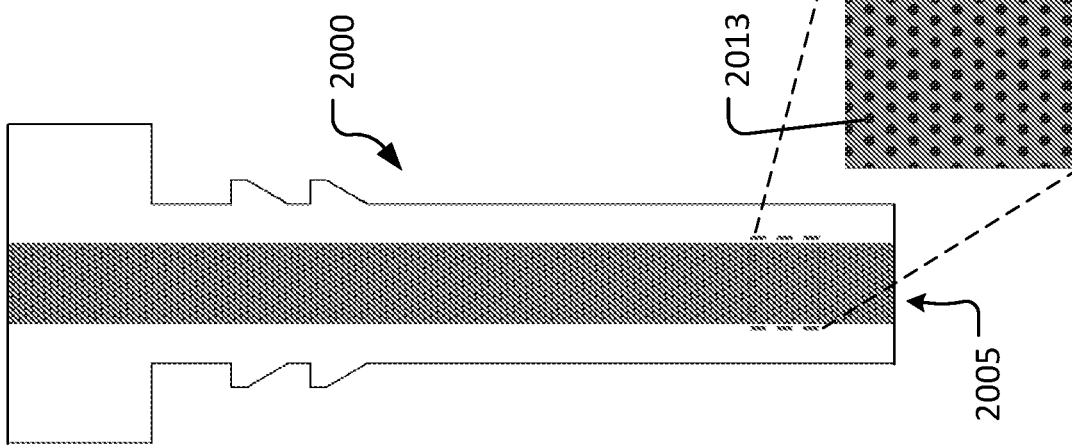
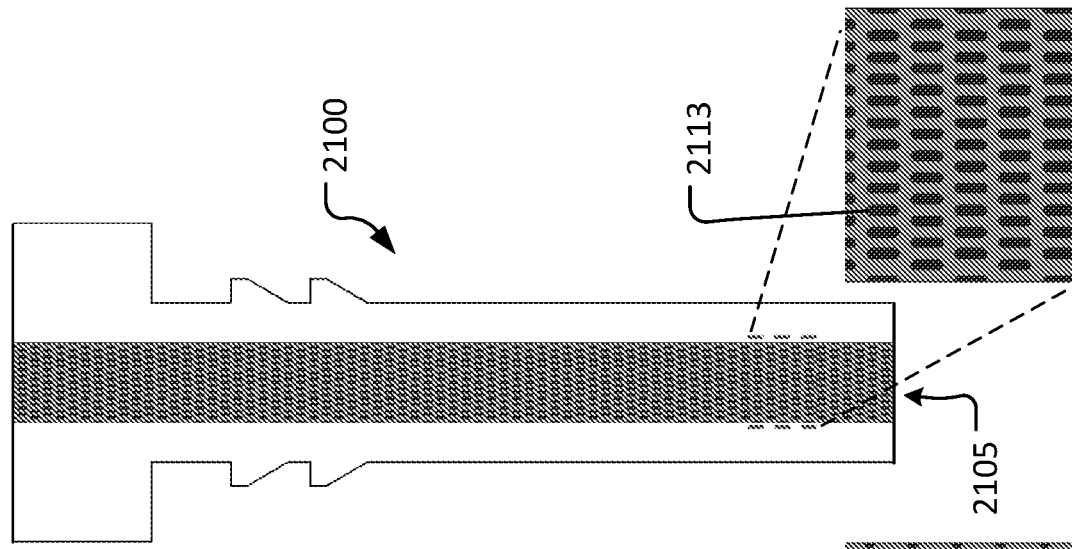

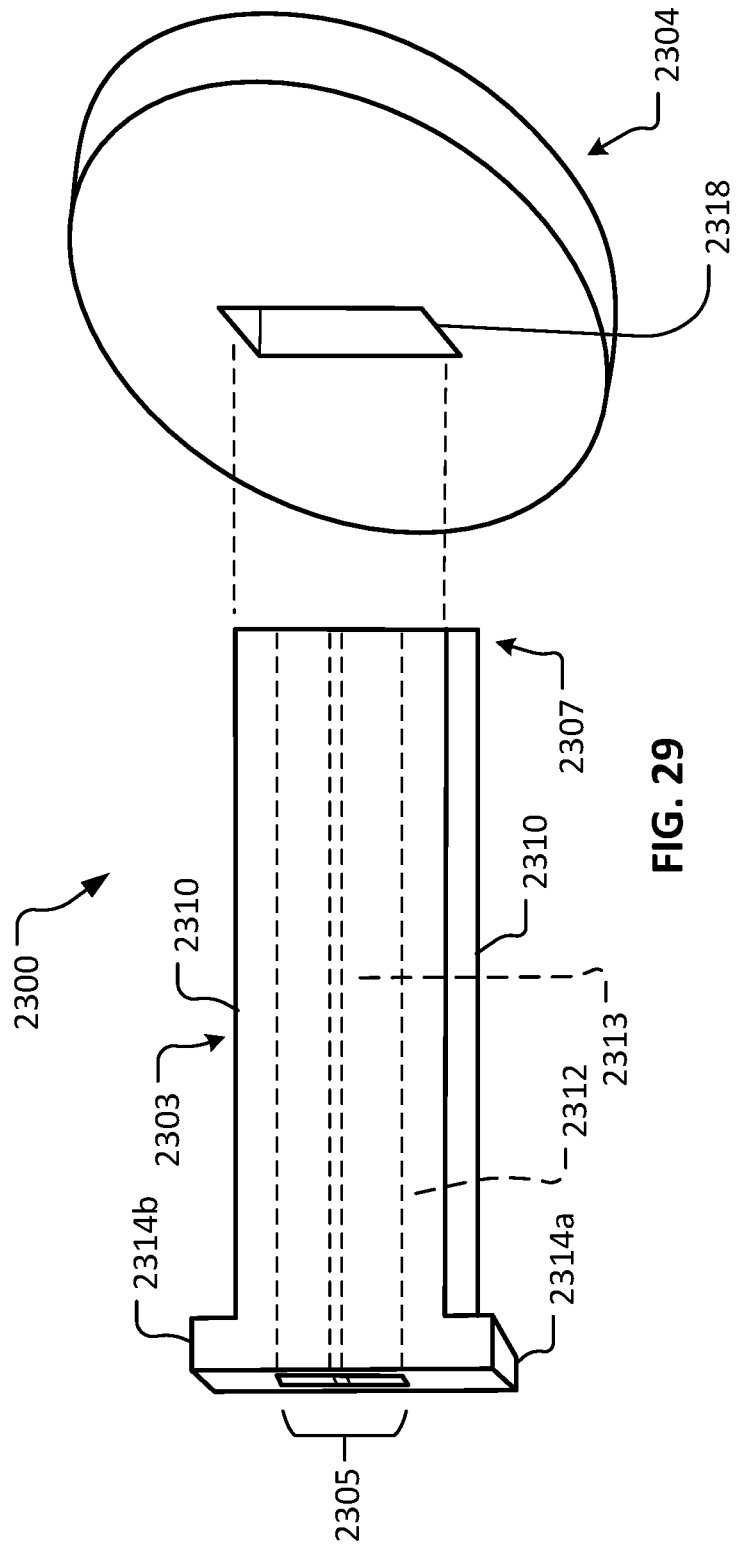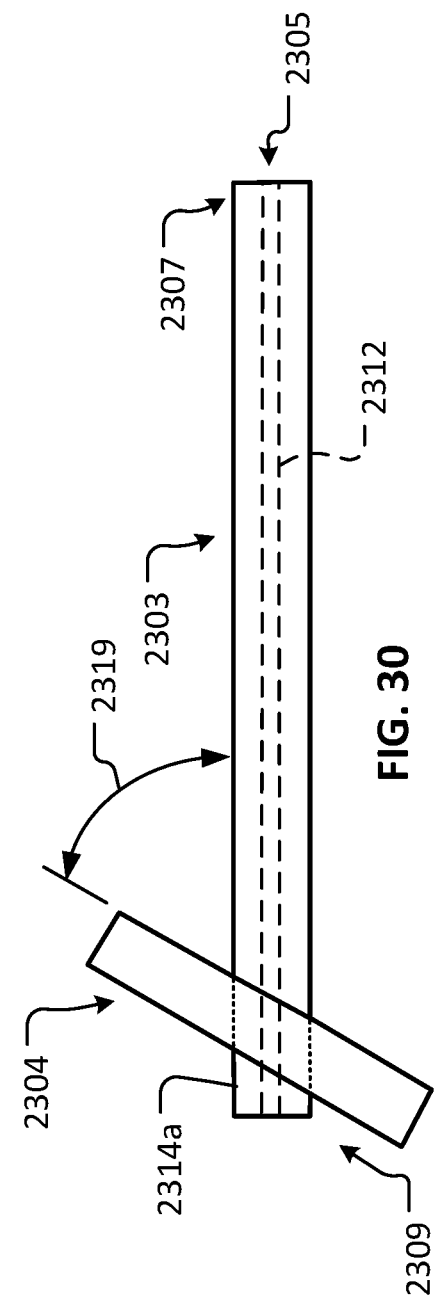
FIG. 29
FIG. 30

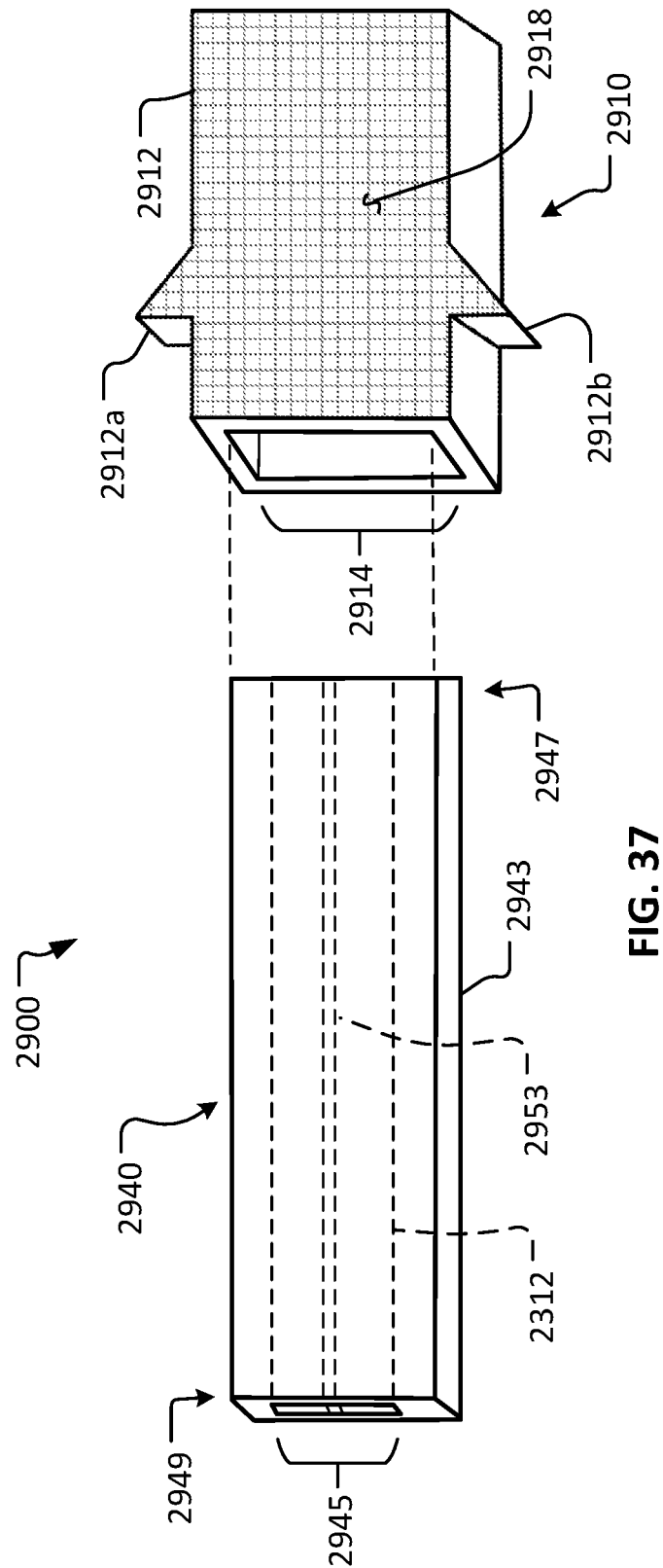
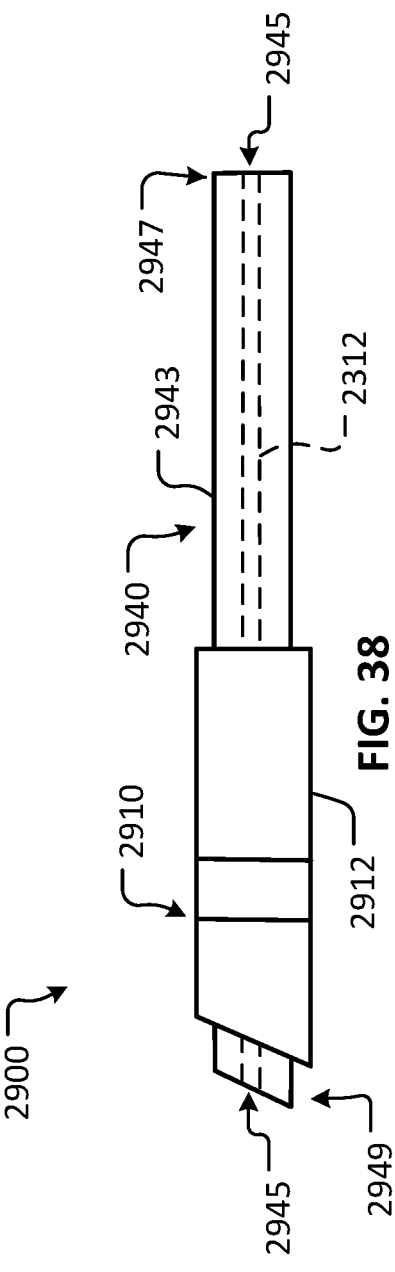
FIG. 37
FIG. 38

GLAUCOMA TREATMENT DEVICES AND METHODS

CROSS REFERENCE TO RELATED APPLICATIONS

This application is a National Stage Application under 35 U.S.C. §371 and claims the benefit of International Application No. PCT/US2015/068017, filed Dec. 30, 2015, which claims the benefit of U.S. Provisional Ser. No. 62/098,609 filed Dec. 31, 2014, and U.S. Provisional Ser. No. 62/235,113 filed Sep. 30, 2015. This disclosure of the prior applications are considered part of (and are incorporated by reference in) the disclosure of this application.

BACKGROUND

1. Technical Field

This document relates to devices and methods for the treatment of glaucoma. For example, this document provides devices configured for implantation into the sclera of an afflicted eye to allow aqueous humor to flow from the anterior chamber of the afflicted eye through a lumen of the device and into the tear film, as well as methods for using such devices to treat glaucoma. This outflow of aqueous humor into the tear film can reduce the intraocular pressure of an afflicted eye in addition to providing moisture and lubrication on to the surface of the eye.

2. Background Information

Glaucoma is the leading cause of irreversible blindness in the world. About 105 million people worldwide have glaucoma, and nearly 10 million are bilaterally blind from this disease. In the United States, over 3 million people suffer from glaucoma, and it is the third most common reason for adults to visit a medical doctor. Elevated intraocular pressure is the outstanding risk factor for the development of glaucoma, and the main reason for progression of the disease. Accordingly, one mode for treatment of glaucoma is directed to lowering the intraocular pressure in the affected eye.

SUMMARY

This document provides devices and methods for the treatment of glaucoma. For example, this document provides devices configured for implantation into the sclera of an afflicted eye to allow aqueous humor to flow from the anterior chamber of the afflicted eye through a lumen of the device and into the tear film, as well as methods for using such devices to treat glaucoma. By the strategic selection of particular materials of construction, and/or by controlling the shape and size of the lumen, in some embodiments, a device provided herein can be filterless, or can be designed to include a filter. A filterless glaucoma treatment device described herein, or a glaucoma treatment device having a filter as described herein, can be designed to prevent bacterial ingress and to provide a desired level of outflow resistance to achieve a desired intraocular pressure (typically a low to normal, or slightly above normal intraocular pressure) in glaucoma patients. Simultaneously, moisture and lubrication is provided to the surface of the eye to alleviate the dry eye symptoms commonly associated with glaucoma.

In one implementation, a device for treating glaucoma in an eye includes a body defining a lumen and having first and second ends, and external and lumenal surfaces. The body has a length sufficient to provide fluid communication between an anterior chamber and a tear film of the eye through the lumen when the device is implanted in a sclera of the eye. The body may include a suture attachment feature configured for receiving a suture to attach the body to the eye.

In another implementation, a device for treating glaucoma in an eye includes a body defining a lumen and having first and second ends, and external and lumenal surfaces. The body has a length sufficient to provide fluid communication between an anterior chamber and a tear film of the eye through the lumen when the device is implanted in a sclera of the eye. The body includes at least one lateral wing that includes a suture attachment feature configured for receiving a suture to attach the body to the eye.

In another implementation, a device for treating glaucoma in an eye includes a body defining a lumen and having first and second ends, and external and lumenal surfaces. The body has a length sufficient to provide fluid communication between an anterior chamber and a tear film of the eye through the lumen when the device is implanted in a sclera of the eye. The lumen is open from the first end to the second end, and is configured to maintain a desired intraocular pressure without having a porous element inside the lumen.

In another implementation, a device for treating glaucoma in an eye includes a body defining a lumen and having first and second ends, and external and lumenal surfaces. The body has a length sufficient to provide fluid communication between an anterior chamber and a tear film of the eye through the lumen when the device is implanted in a sclera of the eye. The body may include one or more ribs extending longitudinally through at least a portion of the lumen, separating the lumen into open channels.

Any one or more of the device implementations described above may optionally include one or more of the following features. The second end may be flared. The lumen may be open from the first end to the second end and configured to maintain a desired intraocular pressure without a porous element inside the lumen. The body may include one or more ribs extending longitudinally through at least a portion of the lumen. The lumenal surface of the device may include a hydrophilic material. The hydrophilic material may include polyethylene glycol. The external surface of the device may be coated with a hetero-bifunctional crosslinker to stimulate collagen binding. The hetero-bifunctional crosslinker may be 5-azido-2-nitrobenzoic acid N-hydroxysuccinimide. In some embodiments, a porous element (e.g., a filter material and the like) is positioned in the lumen.

In another implementation, a method for treating glaucoma includes providing any one of the devices described herein, and implanting the device in the sclera of the eye such that aqueous humor flows from the anterior chamber to the tear film of the eye.

Such a method may optionally include one or more of the following features. After implanting the device, the second end may protrude from the eye by a distance in the range from about 100 µm to about 500 µm, or from about 50 µm to about 1000 µm. Such protrusion can be tolerated by a patient, as with each blink the rectus muscles retract the eyeball by about 1000 µm. A portion of the second end may be flared or otherwise extended, and a surface of the flared or extended portion may be in contact with the eye and generally follow a contour of the eye.

Particular embodiments of the subject matter described in this document can be implemented to realize one or more of the following advantages. In some embodiments, the devices provided herein drain aqueous humor into the tear film, rather than into the subconjuctival space. Therefore, no conjunctival bleb is formed, and therefore there is no potential to scar. Aqueous humor can be expelled into the tear film, thereby enhancing moisture and lubrication to the surface of the eye. Drainage of aqueous humor from the subject device into the tear film can alleviate dry eye symptoms in the glaucoma patients in which it is implanted. In some embodiments, the lumen of the devices provided herein is sized and/or provided with a surface chemistry to resist bacteria ingress. In addition, the geometry of the lumen can be selected to provide a particular aqueous humor outflow resistance that yields desirable intraocular pressure. By the selection of such a geometry, a filterless construct is facilitated in some embodiments. In some embodiments, a filter or filter-like element is included in the lumen. In some embodiments, the materials used to make a device provided herein can be selected to provide bulk biocompatibility by seeking to match scleral rigidity, and/or by providing a porous cellular ingrowth surface on the portion of the device that is in contact with eye tissue. In some embodiments, naturally occurring extracellular matrix proteins such as collagen type 1, laminin, fibronectin, or other cell adhesion peptides (CAPs) can be grafted onto the outer surface to promote biointegration. In some cases, the inner or outer surfaces of the device can be coated with materials such as polymer coatings or biologically active molecules, to promote surface biocompatibility and/or immobilization of the implanted device. Biointegration and scleral rigidity matching can serve to limit inflammation by limiting micromotion of the device. In some embodiments, suture attachment features can be included to allow for device stabilization before and during biointegration. In some embodiments, a protruding portion of the devices provided herein can be flanged or otherwise extended. Such flanged or extended portions may provide various benefits such as (i) providing a bolster to resist forces pushing the device in one direction or another, thereby, e.g., resisting tipping or migration of the device, (ii) resisting growth of conjunctiva over the exposed end of the device, and (iii) providing an insertion depth control.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 2 is a perspective view of an example device for treating glaucoma in accordance with some embodiments.

FIG. 3 is a longitudinal cross-sectional view of the device of FIG. 2.

FIG. 6 is a perspective view of another example device for treating glaucoma in accordance with some embodiments.

FIG. 7 is a side view of the device of FIG. 6.

FIG. 9 is a perspective view of another example device for treating glaucoma in accordance with some embodiments.

FIG. 10 is a side view of the device of FIG. 9.

FIG. 11 is a perspective view of another example device for treating glaucoma in accordance with some embodiments.

FIG. 12 is a side view of the device of FIG. 11.

FIG. 13 is a perspective view of another example device for treating glaucoma in accordance with some embodiments.

FIG. 14 is a side view of the device of FIG. 13.

FIG. 15 is a plan view of another example device for treating glaucoma in accordance with some embodiments. An enlarged view of a portion of the lumenal structure is illustrated.

FIG. 16 is a plan view of another example device for treating glaucoma in accordance with some embodiments. An enlarged view of a portion of the lumenal structure is illustrated.

FIG. 17 is a plan view of another example device for treating glaucoma in accordance with some embodiments. An enlarged view of a portion of the lumenal structure is illustrated.

FIG. 18 is a plan view of another example device for treating glaucoma in accordance with some embodiments. An enlarged view of a portion of the lumenal structure is illustrated.

FIG. 19 is a plan view of another example device for treating glaucoma in accordance with some embodiments. An enlarged view of a portion of the lumenal structure is illustrated.

FIG. 20 is a plan view of another example device for treating glaucoma in accordance with some embodiments. An enlarged view of a portion of the lumenal structure is illustrated.

FIG. 21 is a plan view of another example device for treating glaucoma in accordance with some embodiments. An enlarged view of a portion of the lumenal structure is illustrated.

FIG. 22 is a plan view of another example device for treating glaucoma in accordance with some embodiments. An enlarged view of a portion of the lumenal structure is illustrated.

FIG. 23 is a plan view of another example device for treating glaucoma in accordance with some embodiments. An enlarged view of a portion of the lumenal structure is illustrated.

FIG. 24 is a plan view of another example device for treating glaucoma in accordance with some embodiments. An enlarged view of a portion of the lumenal structure is illustrated.

FIG. 25 is a plan view of another example device for treating glaucoma in accordance with some embodiments. An enlarged view of a portion of the lumenal structure is illustrated.

FIG. 26 is a plan view of another example device for treating glaucoma in accordance with some embodiments. An enlarged view of a portion of the lumenal structure is illustrated.

FIG. 29 is an exploded perspective view of another example device for treating glaucoma in accordance with some embodiments.

FIG. 30 is a side view of the device of FIG. 29.

FIG. 37 is an exploded perspective view of another example device for treating glaucoma in accordance with some embodiments.

FIG. 38 is a side view of the device of FIG. 37.

Like reference numbers represent corresponding parts throughout.

DETAILED DESCRIPTION

This document provides devices and methods for the treatment of glaucoma. For example, this document provides devices configured for implantation into the sclera of an afflicted eye to allow aqueous humor to flow from the anterior chamber of the afflicted eye through a lumen of the device and into the tear film, as well as methods for using such devices to treat glaucoma. By the strategic selection of particular materials of construction, and/or by controlling the shape and size of the lumen, in some embodiments, a device provided herein can be filterless, or can be designed to include a filter. A filterless glaucoma treatment device described herein, or a glaucoma treatment device having a filter as described herein, can be designed to prevent bacterial ingress and to provide a desired level of outflow resistance to achieve a desired intraocular pressure (typically a low to normal, or slightly above normal intraocular pressure) in glaucoma patients. The flow of aqueous humor from the anterior chamber also provides moisture and lubrication to the surface of the eye to alleviate the dry eye symptoms commonly associated with the use of eye drops for treating glaucoma.

Figure 1:
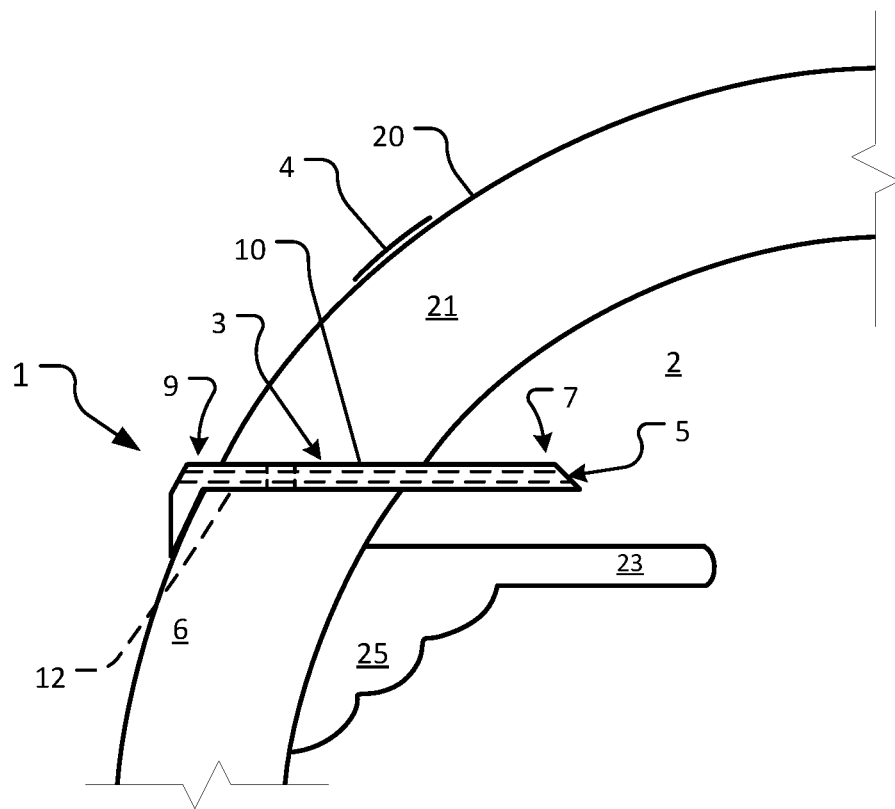
FIG. 1 is a sagittal cross-sectional schematic diagram of an eye with one embodiment of a device illustrative of the devices provided herein implanted in the eye.

Referring to FIG. 1, an example device 1 is shown implanted in an afflicted eye 20 for the purpose of treating glaucoma of afflicted eye 20. The depicted anatomical features of eye 20 include an anterior chamber 2, a sclera 6, a tear film 4, an iris 23, a ciliary body 25, and a cornea 21. Device 1 includes a body 3 that defines a lumen 5. Body 3 includes a first end 7 and a second end 9. Body 3 has an external surface 10, and a lumenal surface 12.

As depicted, device 1 is configured to be surgically implanted in sclera 6 of eye 20. Device 1 has a length sufficient to provide fluid communication between anterior chamber 2 and tear film 4 of eye 20 when device 1 is implanted in sclera 6. As described further herein, in some embodiments, lumen 5 can be sized and configured to provide an appropriate outflow resistance to modulate aqueous humor flowing through lumen 5, without an element that provides additional flow resistance (e.g., a filter or a porous element). In doing so, lumen 5 functions to maintain a desired intraocular pressure (IOP) to treat a glaucoma-afflicted eye 20, while also providing moisture and lubrication to the surface of eye 20 and tear film 4. In other words, aqueous humor is shunted directly to tear film 4. No conjunctival bleb is formed. Additionally, no episcleral venous pressure (EVP) is created that could raise nocturnal IOP. EVP is unaffected by the use of the devices and methods provided herein. In some cases, a device provided herein can define a lumen that includes a filter or a porous element.

In some cases, to provide fluid communication between anterior chamber 2 and tear film 4, device 1 has a length of about 2.5 mm. In some embodiments, device 1 has a length of between about 2.5 mm and about 5.0 mm, or between about 3.5 mm and about 6.0 mm. The length of at least about 2.5 mm will reduce the possibility of blockage of the lumenal opening in anterior chamber 2 by iris 23. The length of device 1 within the scleral tract would preferably be greater than the scleral thickness, because insertion would not be perpendicular to sclera 6 (but more tangential) to be parallel to iris 23.

Referring also to FIGS. 2 and 3, additional details and features of example device 1 are visible therein. FIG. 3 is a longitudinal cross-sectional view of device 1 along section line 3-3 as shown in FIG. 2. It should be understood that one or more (or all) of the details and features described herein in reference to example device 1 are also applicable to the other device embodiments provided herein.

In some embodiments, the main structure of body 3 is formed of a material such as, but not limited to, SU-8, parylene, thiolene, silicone, acrylic, polyimide, polypropylene, polymethyl methacrylate, polyethylene terephthalate (PET), polyethylene glycol (PEG), and expanded polytetrafluoroethylene (e.g., denucleated and coated with laminin). In some embodiments, the main structure of body 3 is formed of a combination of two or more materials. For example, in some embodiments, a layer of PEG is sandwiched between an upper layer of PET and a lower layer of PET. The PEG can be used to define lumen 5, in some embodiments. The use of PEG for the surfaces of the lumen can be advantageous because PEG resists bacterial, protein, and cell adherence.

In some embodiments, a portion of external surface 10 of body 3 is coated with a coating such as a silicone coating or other type of coating. In some embodiments, substantially the entire external surface 10 is coated with a coating such as a silicone coating or other type of coating. In particular embodiments, one portion of external surface 10 may be coated with silicone, and other one or more portions may be coated with another type or types of coatings. Embodiments that include a silicone coating on portions or all of external surface 10 may be coated with a layer of silicone about 50 µm thick, or within a range from about 40 µm to about 60 µm thick, or within a range from about 30 µm to about 70 µm thick, or within a range from about 20 µm to about 80 µm thick, or thicker than about 80 µm.

In some embodiments, external surface 10 of body 3 includes a porous cellular ingrowth coating on at least a portion thereof. In some embodiments, the portion of external surface 10 that is coated with the cellular ingrowth coating corresponds substantially to the portion of body 3 in contact with eye tissue (e.g., sclera 6) following scleral implantation. Such porous cellular ingrowth coatings have been described with respect to other ophthalmic implants, and can be made of silicone with a thickness of about 0.04 mm, in some examples. In some embodiments, surface laser engraving can be used to make depressions in a portion of the body surface to allow cellular ingrowth. Selected growth factors may be adsorbed on to this coating to enhance cellular ingrowth. Coating external surface 10 with a hetero-bifunctional crosslinker allows the grafting of naturally occurring extracellular matrix proteins such as collagen type 1, laminin, fibronectin, or other cell adhesion peptides (CAPs) to external surface 10. These can attract fibroblasts from the episclera to lead to collagen immobilization of device 1. One example of a hetero-bifunctional crosslinker that is useful for such a purpose is 5-azido-2-nitrobenzoic acid N-hydroxysuccinimide.

In some embodiments, one or more portions of body 3 may be configured to inhibit conjunctival overgrowth. For example, second end 9 (of which at least a portion thereof extends exterior to cornea 21) can be configured to inhibit conjunctival overgrowth. Preventing such conjunctival overgrowth can advantageously facilitate patency of lumen 5. In some such embodiments, a coating such as a PEG coating can be applied to second end 9 to inhibit conjunctival overgrowth.

In some embodiments, a bio-inert polymer is included as a liner of lumen 5. That is, in some embodiments, lumenal surface 12 includes a bio-inert polymer material. For example, in some embodiments, a material such as, but not limited to, polyethylene glycol (PEG), phosphoryl choline (PC), or polyethylene oxide (PEO) can be used for the lumenal surface 12 of lumen 5. Such bio-inert surfaces may be further modified with biologically active molecules such as heparin, spermine, surfactants, proteases, or other enzymes, or other biocompatible chemicals amendable to surface immobilization or embedding. Some such materials are advantageously hydrophilic. For example, in some embodiments, the hydrophilic properties of lumenal surface 12 can help prevent bacterial contamination of device 1.

In some embodiments, a filter or filter-like porous member is included in the device's flow path (e.g., lumen 5) for the aqueous humor. In some embodiments, no filter or porous member is present in lumen 5 for the purpose of resisting ingress of bacteria. In some cases, the surface chemistry of lumen 5 of a device provided herein can be used to prevent bacterial ingress. For example, the high molecular weight PEG lining lumen 5 can be very hydrophilic and can attract a hydration shell. The motility of the PEG side chains, and steric stabilization involving these side chains, also can repulse bacteria, cells, and proteins. In some cases, the shear stress of the laminar flow of the aqueous humor as it leaves eye 20 can resist ingress of bacteria into device 1. Experiments demonstrated that when perfusing device 1 into an external broth with $10^8$ bacteria per mL, no bacteria entered device 1. Tears are usually quite sterile and have IgA, lysozyme, lactoferrin, and IgG/complement if inflamed. In some cases, tears can be used to clear an infection.

In some embodiments, device 1 is constructed using bulk and surface micro-machining. In some embodiments, device 1 is constructed using 3D micro-printing. In particular embodiments, external surface 10 is textured such as by stippling, cross-hatching, waffling, roughening, placing backwards facing barbs or protrusions, and the like. One way to accomplish this external surface texturing is by laser engraving. Such featuring can stabilize device 1 in situ and also can increase the visibility of device 1 by making it less transparent. The featuring of the external surface 10 can make device 1 more visible to a surgeon, thereby making the handling and deployment process of device 1 more efficient and convenient.

In some embodiments, the width W of device 1 is in a range from about 0.7 mm to about 1.0 mm, or from about 0.9 mm to about 1.2 mm, or from about 1.1 mm to about 1.4 mm, or from about 1.3 mm to about 1.6 mm, or from about 1.5 mm to about 1.8 mm, or greater than about 1.8 mm.

In the depicted embodiment, body 3 flares and/or extends out around at least part of second end 9. The flaring of body 3 at its second end 9 provides a number of advantages. For example, flaring of body 3 at its second end 9 aids in the surface mounting of device 1 in eye 20 by providing an endpoint of insertion as device 1 is pushed into sclera 6 during surgery. Additionally, the flaring of body 3 at its second end 9 provides structural support to bolster the portion of device 1 that protrudes from eye 20. Such structural support can help maintain patency of lumen 5 by resisting deflection of the protruding portion, which may tend to occur from the forces exerted by an eyelid, for example. For instance, such a posteriorly placed flare/extension bolsters the device against posterior pressures. In some cases, the flaring/extending of body 3 at its second end 9 provides additional resistance to growth of conjunctiva over the exposed second end 9. For example, the additional surface area provided by the flared portion may tend to make growth of conjunctiva over the exposed second end 9 less likely to occur, thereby helping to maintain patency of lumen 5.

In some cases, device 1 can be anteriorly beveled at its first end 7 to assist in implantation and to keep the iris from plugging the inner lumenal opening.

In the depicted embodiment, lumen 5 is a narrow slit with a generally rectangular cross-section. This narrow slit may contain a number of longitudinal channels, which themselves may be square, rectangular, circular, or the like, and combinations thereof. In some embodiments, the total width of lumen 5 is about 0.5 mm. In some embodiments, the total width of lumen 5 is in a range from about 0.4 mm to about 0.6 mm, or about 0.3 mm to about 0.7 mm, or about 0.2 mm to about 0.8 mm. The height, effective width, configuration, and length of lumen 5 can be selected to provide a total resistance so that a desirably low IOP from about 8 mm Hg to about 12 mm Hg is maintained. This IOP is sometimes called the threshold pressure, which is the IOP at which pressure does not contribute to loss of retinal ganglion cells over and above the normal age-related loss. The devices provided herein for providing glaucoma treatment can be configured to attain the threshold pressure, without inducing hypotony.

The effective width of lumen 5 is that width obtained after subtracting the total width of all the device support ribs 13 (as shown in FIG. 2). In some implementations, it is desirable to achieve a normal aqueous humor outflow resistance of about 3.2 mmHg×min/μL. In some implementations, there is some tolerance in the system, since the aqueous humor outflow even in a glaucomatous eye is rarely zero. In fact, the main natural aqueous humor outflow of the eye, the conventional or trabecular meshwork pathway, is IOP dependent and can modify IOP swings. Poiseuille's equation for laminar flow though a porous media (R=8×viscosity× channel length/channel number×π×channel radius to the fourth power) can be used to determine the combination of lumen dimensions to give the proper resistance to provide the desired IOP.

In the depicted embodiment, device 1 includes a suture attachment feature 11. In the depicted embodiment, suture attachment feature 11 is a through-hole that extends completely through body 3. Suture attachment feature 11 can receive a suture therethrough, whereby body 3 is attached to eye 20. In some implementations, such suture(s) can stabilize device 1 in eye 20 prior to bio-integration of device 1 with eye 20. In some embodiments, one or more other types of suture attachment features are included such as a flange, a slot, a projection, a clamp, and the like. In the depicted embodiment, suture attachment feature 11 is a rectangular hole. In some embodiments, suture attachment feature 11 is a circular hole, ovular hole, or another shape of hole.

In some embodiments, suture attachment feature 11 is sized large enough to receive a 10-0 spatula needle. For example, in some embodiments, the dimensions of suture attachment feature 11 is about 300 μm by about 200 μm. Other appropriate sizes for suture attachment feature 11 can be used.

In some embodiments, one or more longitudinal support ribs 13 is included within lumen 5. Support rib 13 can add structural rigidity to help maintain patency of lumen 5. In some embodiments, support rib 13 includes a series of short discontinuous ribs that are disposed along lumen 5. In some embodiments, no support rib 13 is included.

In some embodiments, longitudinal support ribs 13 can divide lumen 5 into two or more portions (e.g., channels). That is, in some embodiments, lumen 5 of body 3 includes two or more channels (e.g., two, three, four, five, six, or more than six channels). Aqueous outflow can occur through these channels, which may be square, rectangular, circular, and the like, and combinations thereof.

In some embodiments, the portion of body 3 that is in contact with eye tissue following implantation includes one or more barbs designed to engage with tissue upon implantation and provide stability to implanted device 1. The one or more barbs may be formed as part of device body 3 during manufacture, or may be fused or bonded to device body 3 using any appropriate technique.

It should be understood that one or more (or all) of the details and features described herein in reference to example device 1 are also applicable to the other device embodiments provided herein. Moreover, one or more of the device details and features described herein can be combined with one or more other device details and features described herein to create hybrid device constructions, and such hybrid device constructions are within the scope of this disclosure.

Figure 4:
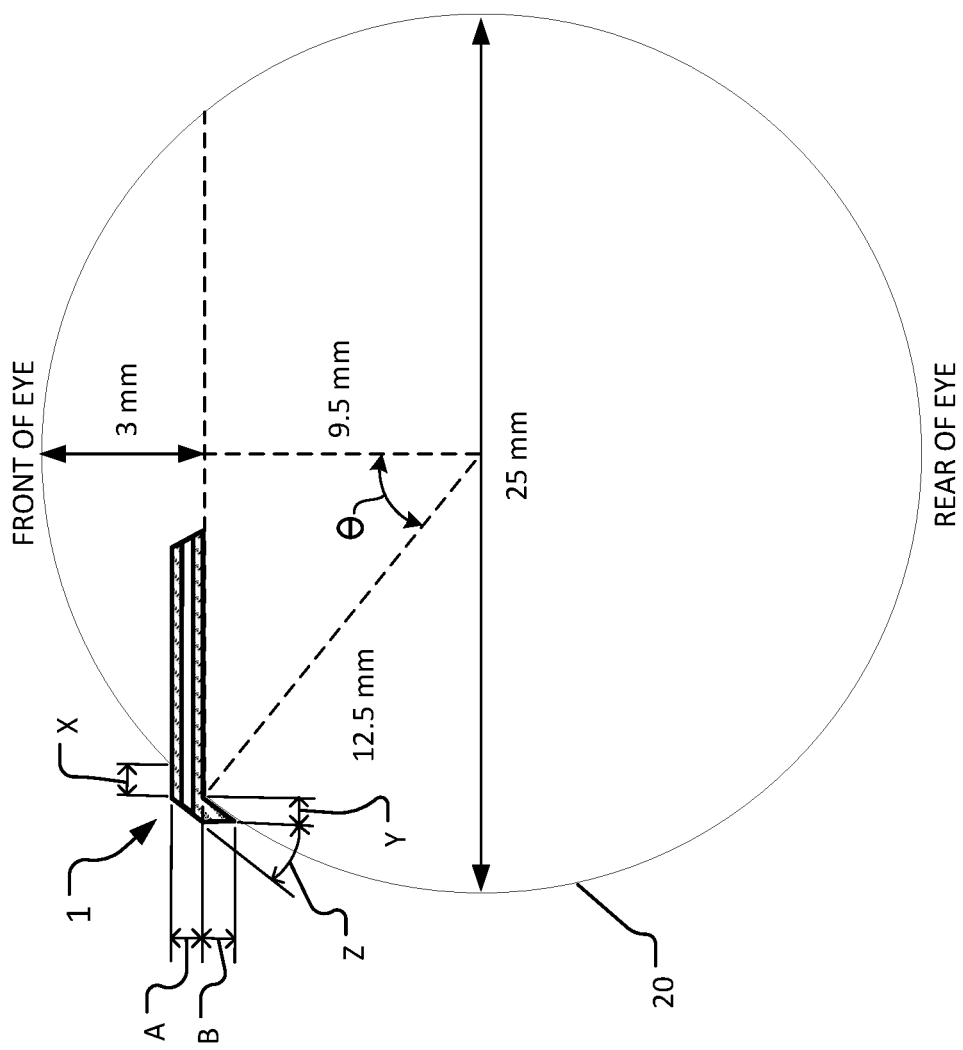
FIG. 4 is a schematic drawing of a sagittal cross-section of an eye (dividing the nasal and temporal halves of the eye) that shows example geometric relationships between the eye and an implanted device for treating glaucoma.

Referring also to FIG. 4, certain geometric aspects of device 1 in relation to eye 20 can be described. Device 1 is shown implanted at the limbus of eye 20. The dimension X is the anterior protrusion of device 1 from the scleral surface, and the dimension Y is the posterior protrusion of device 1 from the scleral surface. In the depicted implementation, dimensions X and Y are about the same because flare bevel angle Z follows the contour of eye 20 (e.g., angle θ is about 40° to 45° in the depicted implementation). The posterior flare and/or extension also follows the contour of eye 20. Protrusion of device 1 from the scleral surface can prevent conjunctival overgrowth. In some cases, this advantage should be balanced with the fact that increased protrusion may tend to make for increased micromotion in some cases. In some embodiments, protrusion dimensions X and Y are in a range from about 50 μm to about 1000 μm, or from about 50 μm to about 200 μm, or from about 100 μm to about 300 μm, or from about 200 μm to about 400 μm, or from about 300 μm to about 500 μm, or from about 400 μm to about 600 μm, or from about 500 μm to about 700 μm, or from about 600 μm to about 800 μm, or from about 700 μm to about 900 μm, or from about 800 μm to about 1,000 μm.

Dimension A in FIG. 4 is the thickness of device 1. Dimension B is the frontal view thickness of the flared portion of device 1. In some embodiments, facial dimensions A and B are about 200 μm. Dimension B can vary in correspondence to variations in selected protrusion dimensions X and Y.

Figure 5:
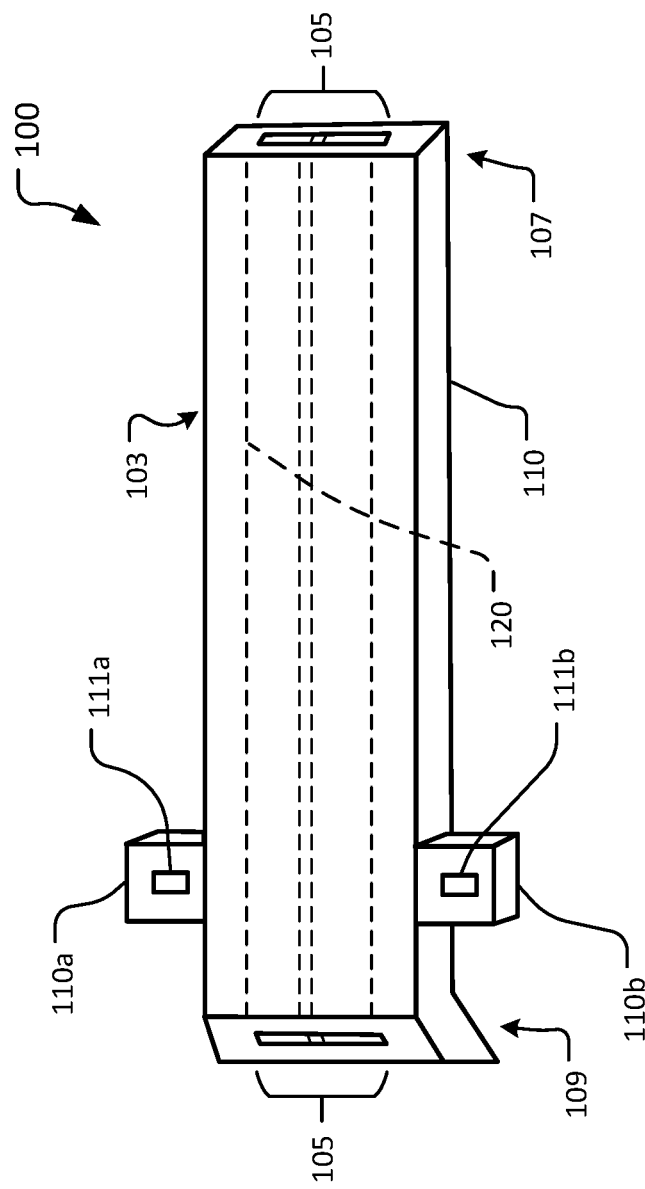
FIG. 5 is a perspective view of another example device for treating glaucoma in accordance with some embodiments.

Referring to FIG. 5, another example device 100 in accordance with some embodiments provided herein is illustrated. Device 100 includes a body 103 that defines a lumen 105. Body 103 includes a first end 107 and a second end 109. Body 103 has an external surface 110 and a lumenal surface 120.

Device 100 can be constructed using any of the materials and techniques as described above in reference to device 1. In some cases, device 100 can be configured and used as described above in reference to device 1. Device 100 differs from device 1, at least in regard to, the addition of lateral wings 110a and 110b. Further, in the depicted embodiment of device 100, device 100 does not include suture attachment feature 11 as included in device 1. Rather, device 100 includes suture attachment features 111a and 111b that are disposed in wings 110a and 110b, respectively. Each of suture attachment features 111a and 111b can be configured like suture attachment feature 11 of device 1 as described above.

A first method for installing the devices provided herein is as follows. Sometime before installation, the eye is irrigated with 1-5% Betadine solution, and topical antibiotic and non-steroidal anti-inflammatory drops (NSAID) are applied to the operative eye. These can be continued for about one week postoperatively four times a day. The NSAID helps stabilize the blood-aqueous barrier.

Each of the embodiments of the device illustrated herein may be inserted under topical anesthesia, possibly supplemented subconjunctivally. In general, the devices provided herein may be inserted into the sclera and under the conjunctiva, using an operative procedure. The location of insertion of a device provided herein can be in the sclera at about the posterior surgical limbus. In some cases, a device provided herein can be inserted at any site around the limbus. In some cases, a device provided herein can be inserted at the superior or temporal limbus.

In some cases, the insertion procedure can begin by excising a small amount of conjunctiva at the site of the anticipated insertion, exposing the underlying sclera. In some cases (as described further below), the insertion procedure is performed without the excision of conjunctiva. Any bleeding can then be cauterized. For embodiments of the device as shown in FIG. 5, a groove incision can be made at the site of insertion with a diamond blade with a depth guard to a depth sufficient to cover the entire length of wings 110a and 110b when the device is in place. Wings 110a and 110b can provide an end-stop for insertion, so the flare at end 109 of device 100 is optional. This groove incision can be made at or near the posterior surgical limbus and can be parallel to the iris plane. For the embodiment of device 1 of FIG. 2, no groove incision is needed, since this is only necessitated by wings 110a and 110b. In some cases, for device 1, only a straight stab incision is used, with the end-stop for insertion depth provided by the flare/extension at the outer end of the device. In some cases, for device 1, insertion can be made through intact conjunctiva.

Approximately 1-2 mm posterior to the limbus, at the site of the now exposed sclera, a diamond blade can be used to make a stab incision into the anterior chamber, while held roughly parallel to the iris. This blade is of a size predetermined to make an opening into the anterior chamber sized appropriately for the introduction of the device. This stab incision is made gently, but relatively quickly, assiduously avoiding any and all intraocular structures. Such an uneventful paracentesis has been found not to disrupt the blood-aqueous barrier in most cases. In any event, any disruption of this barrier is usually of less than 24 hours duration without continued insult.

The device is next picked up and held with a non-toothed forceps. The lips of the stab incision wound may be gaped with a fine, toothed forceps. The pointed tip of the tube element would then be gently pushed through the scleral tract of the stab incision and into the anterior chamber, with the device lying above and parallel to the iris, with the bevel up (i.e., anteriorly). The flare/extension in the embodiments of device 1 and device 100 provide for a definite endpoint to the depth of insertion. For embodiments of the device having a beveled first end, the bevel is oriented anteriorly to minimize the potential for blockage of the lumenal opening by the iris. The scleral barb(s) or other outer surface features (if included) stabilize the device until the biointegration with the sclera is complete. This biointegration is a function of its porous cellular ingrowth surface, possibly enhanced by adsorbed growth factors and/or grafted extracellular matrix proteins. In addition, in some implementations, one or more sutures may be added using the device's suture attachment features to stabilize the device prior to biointegration. For example, in the embodiments of device 1 and device 100, a 10-0 nylon suture on a broad spatula needle may be used to suture the device the sclera, providing additional stability to the device until the biointegration is complete. This suture may then be easily removed at a later time if needed. An alternative insertion technique would have the device pre-loaded into an insertion holder or cartridge, to limit the needed handling of the device by the surgeon. A properly sized sharp blade could be at the leading edge of the inserter, such blade acting also as a guide for implanting the device. Alternatively, the paracentesis could be made with a separate blade, followed by controlled insertion with an inserter.

After insertion of the device, an ocular shield can be placed over the eye. The implanted device will bio-integrate with the sclera, thereby reducing the risks of infections such as tunnel infection.

Referring to FIGS. 6 and 7, another example device 600 in accordance with some embodiments provided herein is illustrated. Device 600 includes a body 603 that defines a lumen 605. Body 603 includes a first end 607 and a second end 609. Body 603 has an external surface 610 and a lumenal surface 612.

Device 600 can be constructed using any of the materials and techniques as described herein in reference to device 1. Also, device 600 can be configured and used in any of the manners described herein in reference to device 1.

In the depicted embodiment, first end 607 is generally orthogonal in relation to the longitudinal surfaces of external surface 610. In contrast, second end 609 of the depicted embodiment is beveled in relation to the longitudinal surfaces of external surface 610. It should be understood that, in some embodiments of device 600 and the other devices provided herein, both ends 607 and 609 may be beveled (e.g., like second end 609), both ends 607 and 609 may be orthogonal (e.g., like first end 607), or either one of ends 607 or 609 may be beveled while the other one of ends 607 or 609 is orthogonal.

In the depicted embodiment, lumen 605 includes a first longitudinal rib 613a and a second longitudinal rib 613b. While in the depicted embodiment, the ribs 613a and 613b extend continuously from first end 607 to second end 609, in some embodiments, ribs 613a and 613b may be made of multiple individually shorter segments and/or other arrangements. It should be understood that lumen 605 may be configured with any of the lumenal constructs provided herein (e.g., FIGS. 15-26, and others), and combinations thereof.

In the depicted embodiment, second end 609 includes a first flange portion 614a and a second flange portion 614b that extend laterally in relation to the longitudinal axis of body 603. In some implementations, surfaces of flange portions 614a and 614b contact the surface of the cornea and provide mechanical stabilization of device 600 in relation to the eye. The outermost lateral surfaces of flange portions 614a and 614b are radiused (contoured) in the depicted embodiment. In some embodiments, the outermost lateral surfaces of flange portions 614a and 614b are planar and parallel to the longitudinal surfaces of external surface 610. In some embodiments, the outer lateral surfaces of flange portions 614a and 614b are planar and unparallel or askew in relation to the longitudinal surfaces of external surface 610.

In some embodiments, one or more suture attachment features are included on device 600 (and the other devices provided herein). In the depicted embodiment, second end 609 includes a first suture attachment structure 616a and a second suture attachment structure 616b. The suture attachment structures 616a and 616b are slots in the depicted embodiment. In some embodiments, other types of suture attachment structures can be alternatively or additionally included. While the depicted embodiment includes two suture attachment structures 616a and 616b, in some embodiments, zero, one, three, four, or more than four suture attachment structures are included.

One or more portions of external surface 610 can be configured for enhanced friction with eye tissue (e.g., the cornea or sclera). Advantageous mechanical stability and/or migration resistance of the device 600 (and the other devices provided herein) in relation to the eye can be facilitated by such portions. For example, in the depicted embodiment, a surface portion 618 includes an enhanced texture (roughness) in comparison to other portions of external surface 610. In the depicted embodiment, surface portion 618 is a waffled surface (cross-hatched). In some embodiments, other types of texturing configurations can be alternatively or additionally included. For example, such texturing configurations can include, but are not limited to, stippling, knurling, inclusion of one or more barbs, and the like, and combinations thereof. In some embodiments, the surface portion 618 is created by techniques such as, but not limited to, laser machining, chemical etching, 3D printing, photo etching, and the like.

Figure 8:
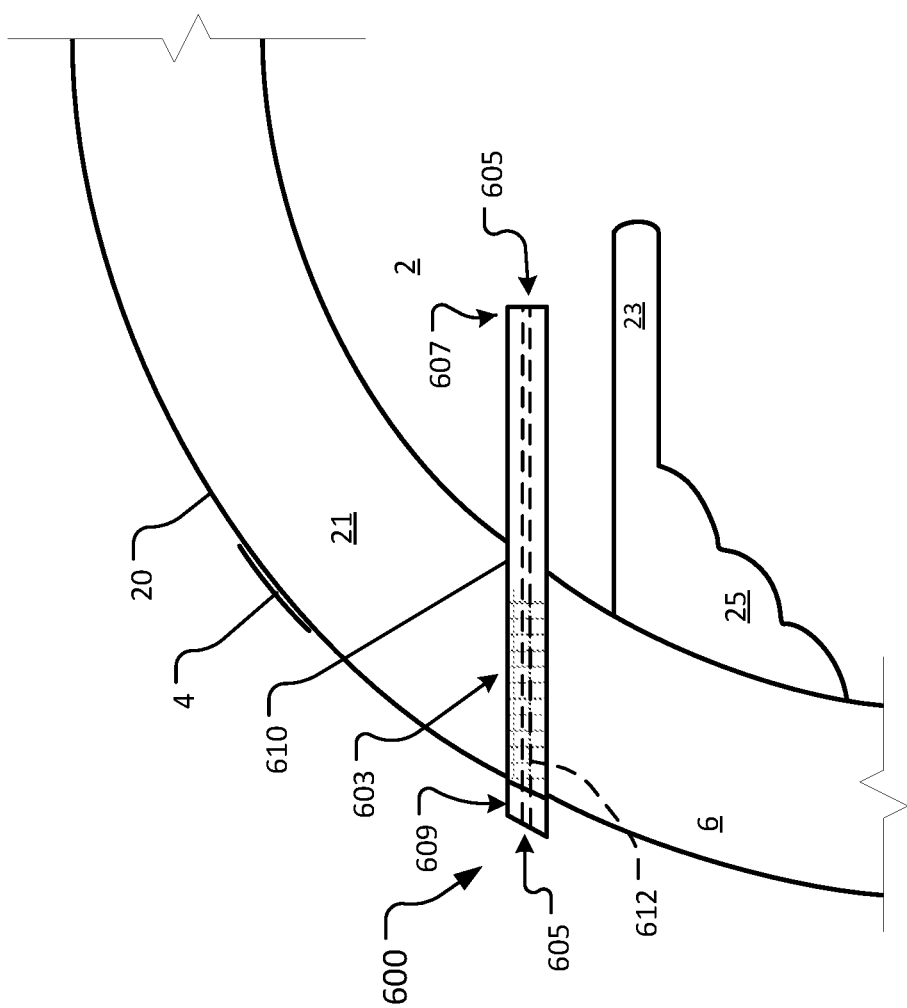
FIG. 8 is a sagittal cross-sectional schematic diagram of an eye with the device of FIG. 6 implanted in the eye.

Referring to FIG. 8, device 600 is shown implanted in afflicted eye 20 for the purpose of treating glaucoma of afflicted eye 20. The depicted anatomical features of eye 20 include anterior chamber 2, sclera 6, tear film 4, iris 23, ciliary body 25, and cornea 21. Device 600 includes body 603 that defines lumen 605. Body 603 includes first end 607 and a second end 609. Body 603 has an external surface 610, and a lumenal surface 612.

As depicted, device 600 (and the other devices provided herein) is configured to be surgically implanted in sclera 6 of eye 20. Device 600 has a length sufficient to provide fluid communication between anterior chamber 2 and tear film 4 of eye 20 when device 600 is implanted in sclera 6. As described further below, in some embodiments lumen 605 is sized and configured to provide an appropriate outflow resistance to modulate aqueous humor flowing through lumen 605, without the need for an element that provides additional flow resistance (e.g., a filter or a porous element). In doing so, lumen 605 functions to maintain a desired IOP to treat a glaucoma afflicted eye 20, while also providing moisture and lubrication to the surface of eye 20 and tear film 4. In some embodiments, a filter or filter-like porous element is includes in lumen 605.

In general, to provide fluid communication between anterior chamber 2 and tear film 4, in some embodiments, device 600 has a length of about 2.5 mm. In some embodiments, device 600 has a length of from about 2.5 mm to about 5.0 mm, or from about 3.5 mm to about 6.0 mm. The length of at least about 2.5 mm will reduce the possibility of blockage of the lumenal opening in anterior chamber 2 by iris 23. The length of device 600 within the scleral tract would preferably be greater than the scleral thickness, because insertion would not be perpendicular to sclera 6 (but more tangential) to be parallel to iris 23.

Referring to FIGS. 9 and 10, another example device 700 in accordance with some embodiments provided herein is illustrated. Device 700 includes a body 703 that defines a lumen 705. Body 703 includes a first end 707 and a second end 709. Body 703 has an external surface 710 and a lumenal surface 712.

Device 700 can be constructed using any of the materials and techniques as described herein in reference to device 1. Also, device 700 can be configured and used in any of the manners described herein in reference to device 1.

In the depicted embodiment, first end 707 is beveled in relation to the longitudinal surfaces of external surface 710. Second end 709 of the depicted embodiment is also beveled in relation to the longitudinal surfaces of external surface 710. It should be understood that, in some embodiments of device 700 (and the other devices provided herein), both ends 707 and 709 may be beveled (e.g., as shown), both ends 707 and 709 may be orthogonal, or either one of ends 707 or 709 may be beveled while the other one of ends 707 or 709 is orthogonal.

In the depicted embodiment, lumen 705 includes a plurality of ovular pillars 713 that are spaced apart from each other. It should be understood that lumen 705 may be configured with any of the lumenal constructs provided herein (e.g., FIGS. 15-26, and others), and combinations thereof.

In the depicted embodiment, second end 709 includes a first flange portion 714a and a second flange portion 714b. In some implementations, flange portions 714a and 714b contact the surface of the cornea and provide mechanical stabilization of device 700 in relation to the eye. The outer lateral surfaces of flange portions 714a and 714b include planar and chamfered portions in the depicted embodiment. In some embodiments, the outer lateral surfaces of flange portions 714a and 714b are radiused (contoured) in relation to the longitudinal surfaces of external surface 710.

In some embodiments, one or more suture attachment features are included on device 700 (and the other devices provided herein). In the depicted embodiment, second end 709 includes a suture attachment structure 716. The suture attachment structure 716 is a slot in the depicted embodiment. In some embodiments, other types of suture attachment structures can be alternatively or additionally included. While the depicted embodiment includes one suture attachment structure 716, in some embodiments, zero, two, three, four, or more than four suture attachment structures are included.

One or more portions of external surface 710 can be configured for enhanced friction with eye tissue (e.g., the cornea or sclera). Such portions can provide advantageous mechanical stability and/or migration resistance of the device 700 (and the other devices provided herein) in relation to the eye. For example, in the depicted embodiment, a surface portion 718 includes an enhanced texture (roughness) in comparison to other portions of external surface 710. In the depicted embodiment, surface portion 718 is a stippled surface. In some embodiments, other types of texturing configurations can be alternatively or additionally included. For example, such texturing configurations can include, but are not limited to, cross-hatching, knurling, inclusion of one or more barbs, and the like, and combinations thereof. In some embodiments, the surface portion 718 is created by techniques such as, but not limited to, laser machining, chemical etching, 3D printing, photo etching, and the like.

Referring to FIGS. 11 and 12, another example device 800 in accordance with some embodiments provided herein is illustrated. Device 800 includes a body 803 that defines a lumen 805. Body 803 includes a first end 807 and a second end 809. Body 803 has an external surface 810 and a lumenal surface 812.

Device 800 can be constructed using any of the materials and techniques as described herein in reference to device 1. Also, device 800 can be configured and used in any of the manners described herein in reference to device 1.

In the depicted embodiment, first end 807 is beveled. Second end 809 of the depicted embodiment is also beveled in relation to the longitudinal surfaces of external surface 810. It should be understood that, in some embodiments of device 800 and the other devices provided herein, both ends 807 and 809 may be orthogonal in relation to the longitudinal surfaces of external surface 810, or either one of ends 807 or 809 may be beveled while the other one of ends 807 or 809 is orthogonal.

In the depicted embodiment, lumen 805 includes a longitudinal rib 813. While in the depicted embodiment, the rib 813 extends continuously from first end 807 to second end 809, in some embodiments, rib 813 may be made of multiple individually shorter segments and/or other arrangements. It should be understood that lumen 805 may be configured with any of the lumenal constructs provided herein (e.g., FIGS. 15-26, and others), and combinations thereof.

In the depicted embodiment, second end 809 includes a first flange portion 814a and a second flange portion 814b. In some implementations, one or more surfaces of flange portions 814a and 814b contact the surface of the cornea and provide mechanical stabilization of device 800 in relation to the eye. The outer lateral surfaces of flange portions 814a and 814b are planar and parallel to the longitudinal surfaces of external surface 810 in the depicted embodiment. In some embodiments, the outer lateral surfaces of flange portions 814a and 814b are contoured. In some embodiments, the outer lateral surfaces of flange portions 814a and 814b are planar and unparallel or askew in relation to the longitudinal surfaces of external surface 810.

In some embodiments, one or more suture attachment features are included on device 800 (and the other devices provided herein). In the depicted embodiment, second end 809 includes a first suture attachment structure 816a and a second suture attachment structure 816b. The suture attachment structures 816a and 816b are holes in the depicted embodiment. In some embodiments, other types of suture attachment structures can be alternatively or additionally included. While the depicted embodiment includes two suture attachment structures 816a and 816b, in some embodiments, zero, one, three, four, or more than four suture attachment structures are included.

One or more portions of external surface 810 can be configured for enhanced friction with eye tissue (e.g., the cornea or sclera). Advantageous mechanical stability and/or migration resistance of the device 800 (and the other devices provided herein) in relation to the eye can be facilitated by such portions. For example, in the depicted embodiment, a plurality of protrusions 818 provide an enhanced texture (greater roughness) in comparison to other portions of external surface 810. In the depicted embodiment, protrusions 818 are disposed on opposing surfaces of external surface 810. It should be understood that protrusions 818 can be located in any desired location(s) on external surface 810. In some embodiments, other types of texturing configurations can be alternatively or additionally included. For example, such texturing configurations can include, but are not limited to, cross-hatching, stippling, knurling, inclusion of one or more barbs, and the like, and combinations thereof. In some embodiments, the surface portion 818 is created by techniques such as, but not limited to, laser machining, chemical etching, 3D printing, photo etching, and the like.

Referring to FIGS. 13 and 14, another example device 900 in accordance with some embodiments provided herein is illustrated. Device 900 includes a body 903 that defines a lumen 905. Body 903 includes a first end 907 and a second end 909. Body 903 has an external surface 910 and a lumenal surface 912.

Device 900 can be constructed using any of the materials and techniques as described herein in reference to device 1. Also, device 900 can be configured and used in any of the manners described herein in reference to device 1.

In the depicted embodiment, first end 907 is not beveled. Rather, first end 907 is generally orthogonal in relation to the longitudinal surfaces of external surface 910. Second end 909 of the depicted embodiment is beveled in relation to the longitudinal surfaces of external surface 910. It should be understood that, in some embodiments of device 900 (and the other devices provided herein), both ends 907 and 909 may be beveled (e.g., like second end 909), both ends 907 and 909 may be orthogonal (e.g., like first end 907), or either one of ends 907 or 909 may be beveled while the other one of ends 907 or 909 is orthogonal.

In the depicted embodiment, lumen 905 includes a first longitudinal rib 913a and a second longitudinal rib 913b. While in the depicted embodiment, the ribs 913a and 913b extend continuously from first end 907 to second end 909, in some embodiments, ribs 913a and 913b may be made of multiple individually shorter segments and/or other arrangements. It should be understood that lumen 905 may be configured with any of the lumenal constructs provided herein (e.g., FIGS. 15-26, and others), and combinations thereof.

In the depicted embodiment, second end 909 includes a first flange portion 914a and a second flange portion 914b. In some implementations, flange portions 914a and 914b contact the surface of the cornea and provide mechanical stabilization of device 900 in relation to the eye. The outer lateral surfaces of flange portions 914a and 914b are planar and parallel to the longitudinal surfaces of external surface 910 in the depicted embodiment. In some embodiments, the outer lateral surfaces of flange portions 914a and 914b are nonplanar (e.g., radiused, chamfered, contoured, etc.). In some embodiments, the outer lateral surfaces of flange portions 914a and 914b are planar and unparallel or askew in relation to the longitudinal surfaces of external surface 910.

In some embodiments, one or more suture attachment features are included on device 900 (and the other devices provided herein). In the depicted embodiment, second end 909 includes a first suture attachment structure 916a and a second suture attachment structure 916b. The suture attachment structures 916a and 916b are slots in the depicted embodiment. In some embodiments, other types of suture attachment structures can be alternatively or additionally included. While the depicted embodiment includes two suture attachment structures 916a and 916b, in some embodiments, zero, one, three, four, or more than four suture attachment structures are included.

One or more portions of external surface 910 can be configured for enhanced friction with eye tissue (e.g., the cornea or sclera). Advantageous mechanical stability and/or migration resistance of the device 900 (and the other devices provided herein) in relation to the eye can be facilitated by such portions. For example, in the depicted embodiment, one or more lateral barbs 918 are included on opposing surfaces of external surface 910. In the depicted embodiment, lateral barbs 918 are triangular protrusions with atraumatic tips (e.g., truncated tips, radiused tips, and the like). In some embodiments, no such lateral barbs 918 are included. In some embodiments, other types of texturing configurations can be alternatively or additionally included. For example, such texturing configurations can include, but are not limited to, stippling, knurling, cross-hatching, and the like, and combinations thereof. In some embodiments, the surface portion 918 is created by techniques such as, but not limited to, laser machining, chemical etching, 3D printing, photo etching, and the like.

FIGS. 15-26 depict various example lumenal structures that can be incorporated in the devices provided herein. It should be understood that the lumenal structures depicted are not an exhaustive compilation of structures that can be used for configuring the lumenal passageways of the devices provided herein. Moreover, the features of one or more of the depicted lumenal structures can be combined with the features of one or more other depicted lumenal structures to create many different combinations, which are within the scope of this disclosure.

The example lumenal structures can be sized and configured to provide an appropriate outflow resistance to modulate aqueous humor flowing through the lumen without the need for an element that provides additional flow resistance (e.g., a filter or a porous element). In doing so, the lumen functions to maintain a desired IOP to treat a glaucoma afflicted eye, while also providing moisture and lubrication to the surface of eye and tear film. In some embodiments, a filter or filter-like porous element is included in the devices provided herein.

Referring to FIG. 15, an example device 1000 can include a lumenal structure 1005 that includes one or more longitudinal ribs 1013. In the depicted embodiment, eight longitudinal ribs 1013 are included. In some embodiments, zero, one, two, three, four, five, six, seven, nine, ten, eleven, twelve, or more than twelve longitudinal ribs 1013 are included. Such longitudinal ribs 1013 serve to divide overall lumen 1005 into two or more longitudinal portions.

Referring to FIG. 16, an example device 1100 can include a lumenal structure 1105 that includes one or more longitudinal rib portions 1113. Such longitudinal rib portions 1113 serve to divide overall lumen 1105 into some segments having two or more longitudinal portions, and some segments that are undivided by longitudinal rib portions 1113. In the depicted embodiment, eight longitudinal rib portions 1113 are included. In some embodiments, zero, one, two, three, four, five, six, seven, nine, ten, eleven, twelve, or more than twelve longitudinal rib portions 1113 are included. Any suitable number of groupings of longitudinal rib portions 1113 can be included.

Referring to FIG. 17, an example device 1200 can include a lumenal structure 1205 that includes one or more longitudinal rib portions 1213. Such longitudinal rib portions 1213 serve to divide overall lumen 1205 into some segments having two or more longitudinal portions, and some segments that are undivided by longitudinal rib portions 1213. In addition, in the depicted embodiment, alternating groupings of longitudinal rib portions 1213 are laterally offset from adjacent groupings of longitudinal rib portions 1213. In the depicted embodiment, eight longitudinal rib portions 1213 are included. In some embodiments, zero, one, two, three, four, five, six, seven, nine, ten, eleven, twelve, or more than twelve longitudinal rib portions 1213 are included. Any suitable number of groupings of longitudinal rib portions 1213 can be included.

Referring to FIG. 18, an example device 1300 can include a lumenal structure 1305 that includes one or more longitudinal ribs 1313. In the depicted embodiment, six longitudinal ribs 1313 are included. In some embodiments, zero, one, two, three, four, five, seven, eight, nine, ten, eleven, twelve, or more than twelve longitudinal ribs 1313 are included. Such longitudinal ribs 1313 serve to divide overall lumen 1305 into two or more longitudinal portions. Longitudinal ribs 1313 can be made to have any suitable width.

Referring to FIG. 19, an example device 1400 can include a lumenal structure 1405 that includes one or more longitudinal rib portions 1413. Such longitudinal rib portions 1413 serve to divide overall lumen 1405 into some segments having two or more longitudinal portions, and some segments that are undivided by longitudinal rib portions 1413. In the depicted embodiment, six longitudinal rib portions 1413 are included. In some embodiments, zero, one, two, three, four, five, seven, eight, nine, ten, eleven, twelve, or more than twelve longitudinal rib portions 1413 are included. Any suitable number of groupings of longitudinal rib portions 1413 can be included. Longitudinal ribs 1313 can be made to have any suitable width.

Referring to FIG. 20, an example device 1500 can include a lumenal structure 1505 that includes one or more longitudinal rib portions 1513. Such longitudinal rib portions 1513 serve to divide overall lumen 1505 into some segments having two or more longitudinal portions, and some segments that are undivided by longitudinal rib portions 1513. In addition, in the depicted embodiment, alternating groupings of longitudinal rib portions 1513 are laterally offset from adjacent groupings of longitudinal rib portions 1513. In the depicted embodiment, six longitudinal rib portions 1513 are included. In some embodiments, zero, one, two, three, four, five, seven, nine, eight, ten, eleven, twelve, or more than twelve longitudinal rib portions 1513 are included. Any suitable number of groupings of longitudinal rib portions 1513 can be included. Longitudinal ribs 1313 can be made to have any suitable width.

Referring to FIG. 21, an example device 1600 can include a lumenal structure 1605 that includes one or more longitudinal ribs 1613. In the depicted embodiment, three longitudinal ribs 1613 are included. In some embodiments, zero, one, two, four, five, six, seven, eight, nine, ten, eleven, twelve, or more than twelve longitudinal ribs 1613 are included. Such longitudinal ribs 1613 serve to divide overall lumen 1605 into two or more longitudinal portions. Longitudinal ribs 1613 can be made to have any suitable width.

Referring to FIG. 22, an example device 1700 can include a lumenal structure 1705 that includes one or more longitudinal rib portions 1713. Such longitudinal rib portions 1713 serve to divide overall lumen 1705 into some segments having two or more longitudinal portions, and some segments that are undivided by longitudinal rib portions 1713. In the depicted embodiment, three longitudinal rib portions 1713 are included. In some embodiments, zero, one, two, four, five, six, seven, eight, nine, ten, eleven, twelve, or more than twelve longitudinal rib portions 1713 are included. Any suitable number of groupings of longitudinal rib portions 1713 can be included. Longitudinal ribs 1713 can be made to have any suitable width.

Referring to FIG. 23, an example device 1800 can include a lumenal structure 1805 that includes one or more longitudinal rib portions 1813. Such longitudinal rib portions 1813 serve to divide overall lumen 1805 into some segments having two or more longitudinal portions, and some segments that are undivided by longitudinal rib portions 1813. In addition, in the depicted embodiment, alternating groupings of longitudinal rib portions 1813 are laterally offset from adjacent groupings of longitudinal rib portions 1813. In the depicted embodiment, three longitudinal rib portions 1813 are included. In some embodiments, zero, one, two, four, five, six, seven, nine, eight, ten, eleven, twelve, or more than twelve longitudinal rib portions 1813 are included. Any suitable number of groupings of longitudinal rib portions 1813 can be included. Longitudinal ribs 1313 can be made to have any suitable width.

Referring to FIG. 21, an example device 1900 can include a lumenal structure 1905 that includes a plurality of circular pillars 1913. Such circular pillars 1913 serve to constrict lumen 1905 but not prevent all flow of fluid through lumen 1905. Circular pillars 1913 can be made to have any suitable size (e.g., diameter). In the depicted embodiment, circular pillars 1913 are longitudinally aligned in rows.

Referring to FIG. 22, an example device 2000 can include a lumenal structure 2005 that includes a plurality of circular pillars 2013. Such circular pillars 2013 serve to constrict lumen 2005 but not prevent all flow of fluid through lumen 2005. Circular pillars 2013 can be made to have any suitable size (e.g., diameter). In the depicted embodiment, circular pillars 2013 are laterally offset from longitudinally adjacent circular pillars 2013.

Referring to FIG. 23, an example device 2100 can include a lumenal structure 2105 that includes a plurality of ovular pillars 2113. Such ovular pillars 2113 serve to constrict lumen 2105 but not prevent all flow of fluid through lumen 2105. Ovular pillars 2113 can be made to have any suitable size (e.g., length and width). In the depicted embodiment, ovular pillars 2113 are laterally offset from longitudinally adjacent ovular pillars 2113.

Figure 27:
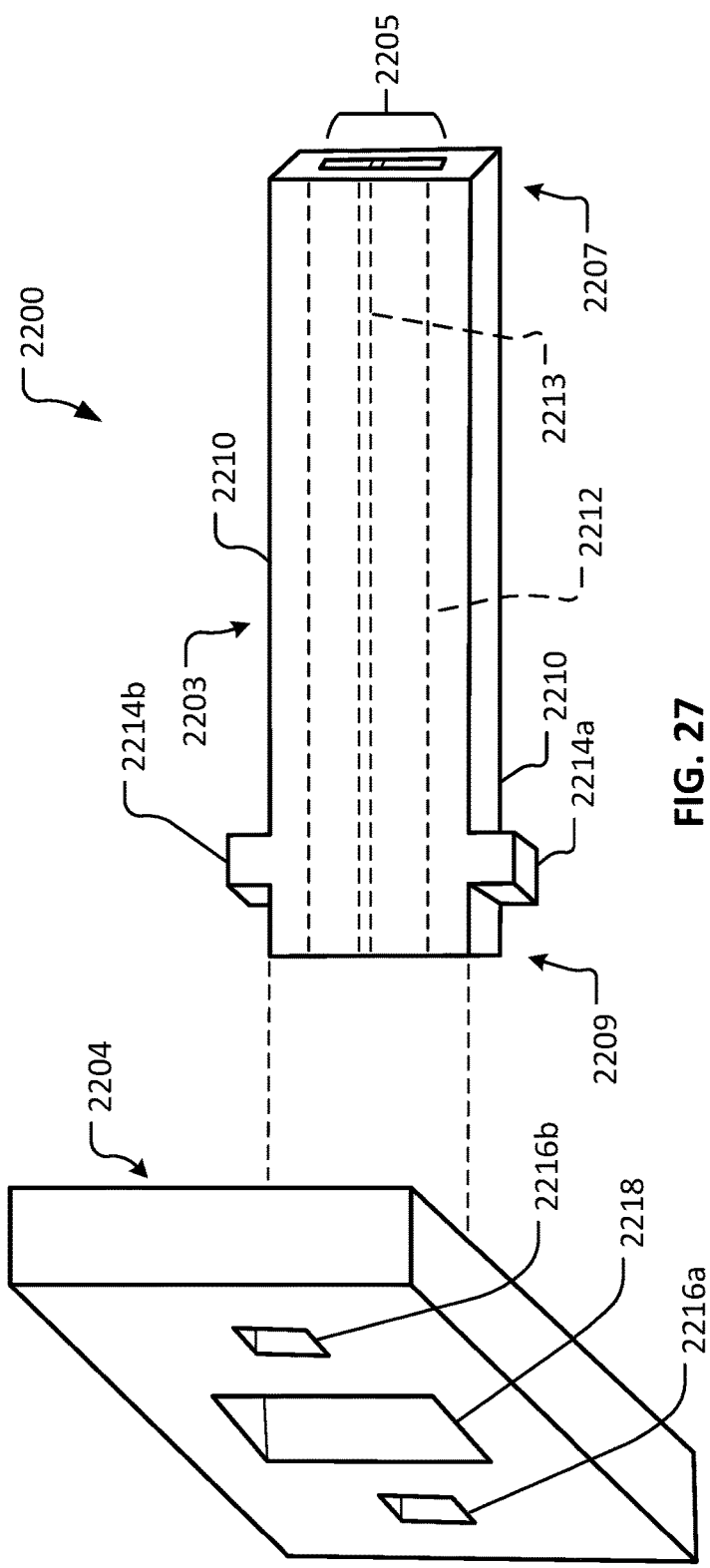
FIG. 27 is an exploded perspective view of another example device for treating glaucoma in accordance with some embodiments.
Figure 28:
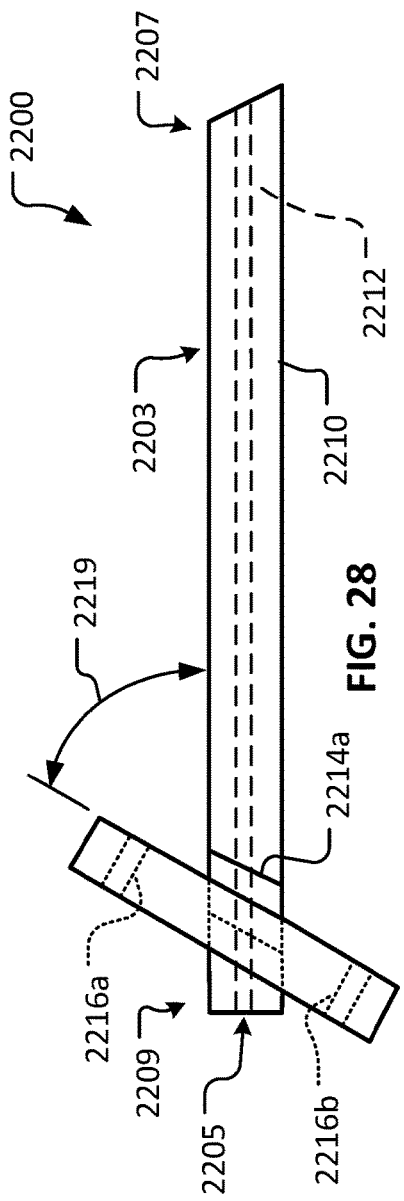
FIG. 28 is a side view of the device of FIG. 27.

Referring to FIGS. 27 and 28, another example device 2200 in accordance with some embodiments provided herein is illustrated. Device 2200 includes a body 2203 that defines a lumen 2205. Body 2203 includes a first end 2207 and a second end 2209. Body 2203 has an external surface 2210, and a lumenal surface 2212. Device 2200 also includes a bolster portion 2204. Bolster portion 2204 can be mated with body 2203. In some cases, second end 2209 of body 2203 can be coupled with receptacle 2218 of bolster portion 2204. In some embodiments, a compression fit (interference fit) exists between body 2203 and bolster portion 2204, such that body 2203 and bolster portion 2204 are held together and effectively function as a monolithic device prior to and after implantation into an eye.

Bolster portion 2204 and body 2203 can be constructed using any of the materials and techniques as described herein in reference to device 1. In addition, in some embodiments, bolster portion 2204, or portions thereof, is made of silicone. In some embodiments, bolster portion 2204, or portions thereof, is made of PET. Device 2200 can be configured and used in any of the manners described herein in reference to device 1.

Bolster portion 2204 provides a stable footing for device 2200 when device 2200 is implanted in an eye. In some cases, at least a portion of bolster portion 2204 contacts the surface of the eye, thereby mechanically stabilizing the device 2200 in relation to the eye. In some cases, bolster portion 2204 can serve to prevent or inhibit tipping of device 2200 in relation to the eye. Other device design features and device use techniques to prevent or inhibit tipping of device 2200 (and the other devices provided herein) in relation to the eye are also envisioned. For example, the inclusion of design features such as barbs, textured surfaces, projections, and other mechanical aspects can be included to prevent or inhibit tipping. Further, in some cases the angle of insertion of the device 200 (and the other devices provided herein) can be selected and/or optimized so prevent or inhibit tipping.

While in the depicted embodiment, bolster portion 2204 is rectangular, in some embodiments, bolster portions with other shapes are used. Such shapes can include, but are not limited to, circles, ovals, squares, parallelograms, and the like. Bolster portion 2219 can be oriented at an angle 2219 in relation to body 2203. In some embodiments, angle 2219 is about a 45° angle. In some embodiments, angle 2219 is within the range from about 40° to about 50°, or from about 35° to about 45°, or from about 45° to about 55°, or from about 30° to about 60°, or from about 20° to about 70°, or from about 10° to about 80°, or from about 0° to about 90°, or greater than about 90°.

In the depicted embodiment, first end 2207 is beveled. In some embodiments, first end 2207 is generally orthogonal in relation to the longitudinal surfaces of external surface 2210. Second end 2209 of the depicted embodiment is not beveled in relation to the longitudinal surfaces of external surface 2210. It should be understood that, in some embodiments of device 2200 and the other devices provided herein, both ends 2207 and 2209 may be beveled (e.g., like first end 2207), both ends 2207 and 2209 may be orthogonal (e.g., like second end 2209), or either one of ends 2207 or 2209 may be beveled while the other one of ends 2207 or 2209 is orthogonal.

In the depicted embodiment, second end 2209 extends beyond bolster portion 2204. In some embodiments, second end 2209 is flush or slightly recessed in relation to bolster portion 2204.

In the depicted embodiment, lumen 2205 includes a longitudinal rib 2213. While in the depicted embodiment, rib 2213 extends continuously from first end 2207 to second end 2209, in some embodiments, rib 2213 may be made of multiple individually shorter segments and/or other arrangements. It should be understood that lumen 2205 may be configured with any of the lumenal constructs provided herein (e.g., FIGS. 15-26, and others), and combinations thereof.

In the depicted embodiment, second end 2209 includes a first flange portion 2214*a* and a second flange portion 2214*b*. In some implementations, flange portions 2214*a* and 2214*b* contact the surface of the cornea and provide mechanical stabilization of device 2200 in relation to the eye. In addition, in this two-piece construct of device 2200, flange portions 2214*a* and 2214*b* engage within recesses of bolster portion 2204 to provide a sturdy mechanical connection therebetween. In the depicted embodiment, flange portions 2214*a* and 2214*b* protrude from bolster portion 2204. In some embodiments, flange portions 2214*a* and 2214*b* are flush or slightly recessed in relation to bolster portion 2204.

In some embodiments, one or more suture attachment features are included on device 2200 (and the other devices provided herein). In the depicted embodiment, bolster portion 2204 includes a first suture attachment structure 2216*a* and a second suture attachment structure 2216*b*. The suture attachment structures 2216*a* and 2216*b* are holes in the depicted embodiment. In some embodiments, other types of suture attachment structures can be alternatively or additionally included. While the depicted embodiment includes two suture attachment structures 2216*a* and 2216*b*, in some embodiments, zero, one, three, four, or more than four suture attachment structures are included.

One or more portions of external surface 2210 can be configured for enhanced friction with eye tissue (e.g., the cornea or sclera) to improve mechanical stability and/or migration resistance of the device 2200 (and the other devices provided herein) in relation to the eye. In some embodiments, configurations of external surface 2210 can include, but are not limited to, stippling, knurling, crosshatching, inclusion of one or more barbs, and the like, and combinations thereof. In some embodiments, some such configurations are created by techniques such as, but not limited to, laser machining, chemical etching, 3D printing, photo etching, and the like.

Referring to FIGS. 29 and 30, another example device 2300 in accordance with some embodiments provided herein is illustrated. Device 2300 includes a body 2303 that defines a lumen 2305. Body 2303 includes a first end 2307 and a second end 2309. Body 2303 has an external surface 2310 and a lumenal surface 2312. Device 2300 also includes a bolster portion 2304. Bolster portion 2304 can be mated with body 2303. In some cases, body 2303 can be coupled with receptacle 2318 of bolster portion 2304 such that flange portions 2314*a* and 2314*b* are positioned in contact with bolster portion 2304. In some embodiments, a compression fit (interference fit) exists between body 2303 and bolster portion 2304, such that body 2303 and bolster portion 2304 are held together and effectively function as a monolithic device prior to and after implantation into an eye.

Bolster portion 2304 and body 2303 can be constructed using any of the materials and techniques as described herein in reference to device 1. In addition, in some embodiments, bolster portion 2304, or portions thereof, is made of silicone. In some embodiments, bolster portion 2304, or portions thereof, is made of PET. Device 2300 can be configured and used in any of the manners described herein in reference to device 1.

Bolster portion 2304 provides a stable footing for device 2300 when device 2300 is implanted in an eye. In some cases, at least a portion of bolster portion 2304 contacts the surface of the eye, thereby mechanically stabilizing the device 2300 in relation to the eye. In some cases, bolster portion 2304 can serve to prevent or inhibit tipping of device 2300 in relation to the eye.

While in the depicted embodiment, bolster portion 2304 is ovular, in some embodiments, bolster portions with other shapes are used. Such shapes can include, but are not limited to, circles, rectangles, squares, parallelograms, and the like. Bolster portion 2319 can be oriented at an angle 2319 in relation to body 2303. In some embodiments, angle 2319 is about a 45° angle. In some embodiments, angle 2319 is within the range from about 40° to about 50°, or from about 35° to about 45°, or from about 45° to about 55°, or from about 30° to about 60°, or from about 20° to about 70°, or from about 10° to about 80°, or from about 0° to about 90°, or greater than about 90°.

In the depicted embodiment, first end 2307 is not beveled. Rather, first end 2307 is generally orthogonal in relation to the longitudinal surfaces of external surface 2310. Second end 2309 of the depicted embodiment is also not beveled in relation to the longitudinal surfaces of external surface 2310. It should be understood that, in some embodiments of device 2300 and the other devices provided herein, both ends 2307 and 2309 may be beveled, both ends 2307 and 2309 may be orthogonal, or either one of ends 2307 or 2309 may be beveled while the other one of ends 2307 or 2309 is orthogonal.

In the depicted embodiment, second end 2309 extends beyond bolster portion 2304. In some embodiments, second end 2309 is flush or slightly recessed in relation to bolster portion 2304.

In the depicted embodiment, lumen 2305 includes a longitudinal rib 2313. While in the depicted embodiment, rib 2313 extends continuously from first end 2307 to second end 2309, in some embodiments, rib 2313 may be made of multiple individually shorter segments and/or other arrangements. It should be understood that lumen 2305 may be configured with any of the lumenal constructs provided herein (e.g., FIGS. 15-26, and others), and combinations thereof.

In the depicted embodiment, second end 2309 includes first flange portion 2314a and second flange portion 2314b. In this two-piece construct of device 2300, flange portions 2314a and 2314b engage with bolster portion 2304 to provide a sturdy mechanical connection therebetween. In the depicted embodiment, flange portions 2314a and 2314b protrude from bolster portion 2304. In some embodiments, flange portions 2314a and 2314b are flush or slightly recessed in relation to bolster portion 2304.

In some embodiments, one or more suture attachment features are included on device 2300 (and the other devices provided herein). In the depicted embodiment, bolster portion 2304 does not include any such suture attachment features. In some embodiments, when bolster portion 2304 is made of silicone, bolster portion 2304 can be pierced by a needle to allow sutures to be threaded through bolster portion 2304 (despite the lack of specific suture attachment features). While the depicted embodiment includes no suture attachment structures, in some embodiments, one, two, three, four, or more than four suture attachment structures are included.

One or more portions of external surface 2310 can be configured for enhanced friction with eye tissue (e.g., the cornea or sclera) to improve mechanical stability and/or migration resistance of the device 2300 (and the other devices provided herein) in relation to the eye. In some embodiments, configurations of external surface 2310 can include, but are not limited to, stippling, knurling, cross-hatching, inclusion of one or more barbs, and the like, and combinations thereof. In some embodiments, some such configurations are created by techniques such as, but not limited to, laser machining, chemical etching, 3D printing, photo etching, and the like.

Figure 31:
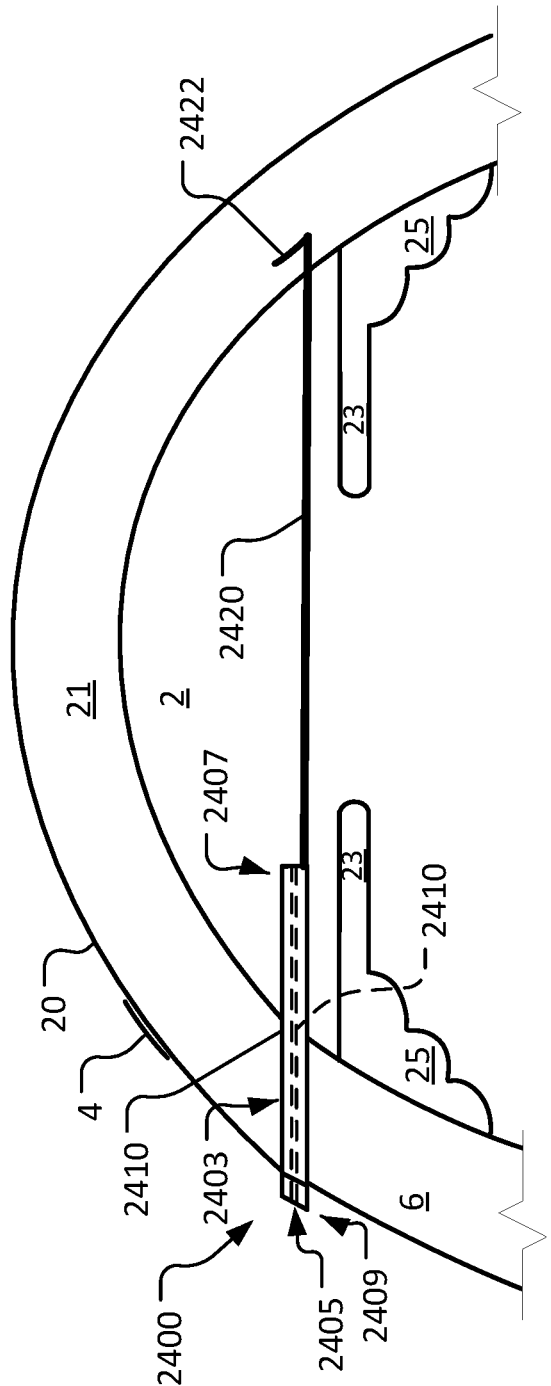
FIG. 31 is a sagittal cross-sectional schematic diagram of an eye with another embodiment of a device illustrative of the devices provided herein implanted in the eye.

Referring to FIG. 31, an example device 2400 is shown implanted in afflicted eye 20 for the purpose of treating glaucoma of afflicted eye 20. The depicted anatomical features of eye 20 include anterior chamber 2, sclera 6, tear film 4, iris 23, ciliary body 25, and cornea 21.

Device 2400 includes body 2403 that defines lumen 2405. Body 2403 includes first end 2407 and a second end 2409. Body 2403 has an external surface 2410, and a lumenal surface 2412.

In the depicted embodiment, device 2400 also includes a longitudinal extension member 2420 that is attached to body 2403. An anchor member 2422 is attached to the opposite end of the extension member 2420. Anchor member 2422 can be a structure such as, but not limited to, a barb, a hook, a screw, a clamp, and the like. Anchor member 2422 can be implanted within or attached to cornea 21 or sclera 6. In some cases, extension member 2420 and anchor member 2422 serve to stabilize mechanically device 2400 in relation to eye 20.

In some embodiments, extension member 2420 is a wire member, or another type of elongate member. In some embodiments, extension member 2420 and anchor member 2422 are made of a metallic material such as nitinol or stainless steel. Alternatively or additionally, in some embodiments, extension member 2420 and anchor member 2422 are made of a polymeric material.

Figure 32:
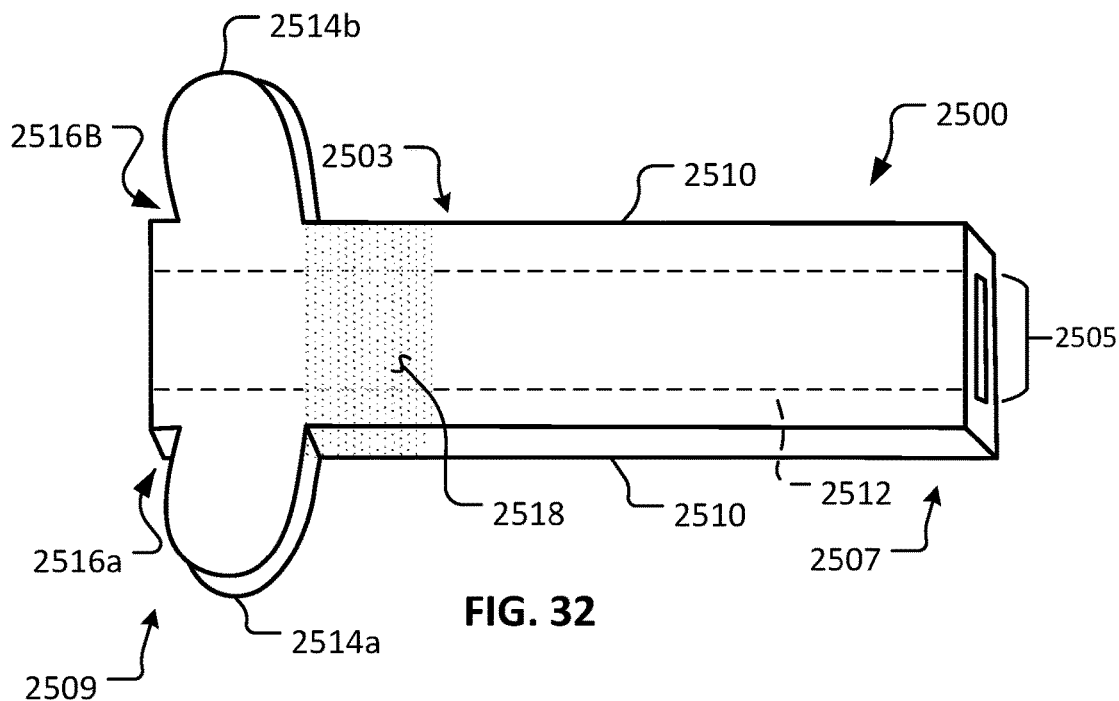
FIG. 32 is a perspective view of another example device for treating glaucoma in accordance with some embodiments.

Referring to FIG. 32, another example device 2500 in accordance with some embodiments provided herein is illustrated. Device 2500 includes a body 2503 that defines a lumen 2505. Body 2503 includes a first end 2507 and a second end 2509. Body 2503 has an external surface 2510 and a lumenal surface 2512.

Device 2500 can be constructed using any of the materials and techniques as described herein in reference to device 1. Also, device 2500 can be configured and used in any of the manners described herein in reference to device 1.

In the depicted embodiment, first end 2507 is beveled. In some embodiments, first end 2507 is generally orthogonal in relation to the longitudinal surfaces of external surface 2510. Second end 2509 of the depicted embodiment is not beveled in relation to the longitudinal surfaces of external surface 2510. It should be understood that, in some embodiments of device 2500 and the other devices provided herein, both ends 2507 and 2509 may be beveled (e.g., like first end 2507), both ends 2507 and 2509 may be orthogonal (e.g., like second end 2509), or either one of ends 2507 or 2509 may be beveled while the other one of ends 2507 or 2509 is orthogonal.

In the depicted embodiment, lumen 2505 is open continuously from first end 2507 to second end 2509. In some embodiments, lumen 2505 can be configured with any of the other lumenal constructs provided herein (e.g., FIGS. 15-26, and others), and combinations thereof.

In the depicted embodiment, second end 2509 includes a first flange portion 2514a and a second flange portion 2514b. In some implementations, flange portions 2514a and 2514b contact the surface of the cornea and provide mechanical stabilization of device 2500 in relation to the eye. The outer lateral surfaces of flange portions 2514a and 2514b are radiused (contoured) in the depicted embodiment. In some embodiments, the outer lateral surfaces of flange portions 2514a and 2514b are planar and parallel to the longitudinal surfaces of external surface 2510. In some embodiments, the outer lateral surfaces of flange portions 2514a and 2514b are planar and unparallel or askew in relation to the longitudinal surfaces of external surface 2510.

In some embodiments, one or more suture attachment features are included on device 2500 (and the other devices provided herein). In the depicted embodiment, second end 2509 includes a first suture attachment structure 2516a and a second suture attachment structure 2516b. The suture attachment structures 2516a and 2516b are grooves in the depicted embodiment. In some embodiments, other types of suture attachment structures can be alternatively or additionally included. While the depicted embodiment includes two suture attachment structures 2516a and 2516b, in some embodiments, zero, one, three, four, or more than four suture attachment structures are included.

One or more portions of external surface 2510 can be configured for enhanced friction with eye tissue (e.g., the cornea or sclera). Advantageous mechanical stability and/or migration resistance of the device 2500 (and the other devices provided herein) in relation to the eye can be facilitated by such portions. For example, in the depicted embodiment, a surface portion 2518 includes an enhanced texture (roughness) in comparison to other portions of external surface 2510. In the depicted embodiment, surface portion 2518 is a stippled surface. In some embodiments, other types of texturing configurations can be alternatively or additionally included. For example, such texturing configurations can include, but are not limited to, cross-hatching, knurling, inclusion of one or more barbs, and the like, and combinations thereof. In some embodiments, the surface portion 2518 is created by techniques such as, but not limited to, laser machining, chemical etching, 3D printing, photo etching, and the like.

Figure 33:
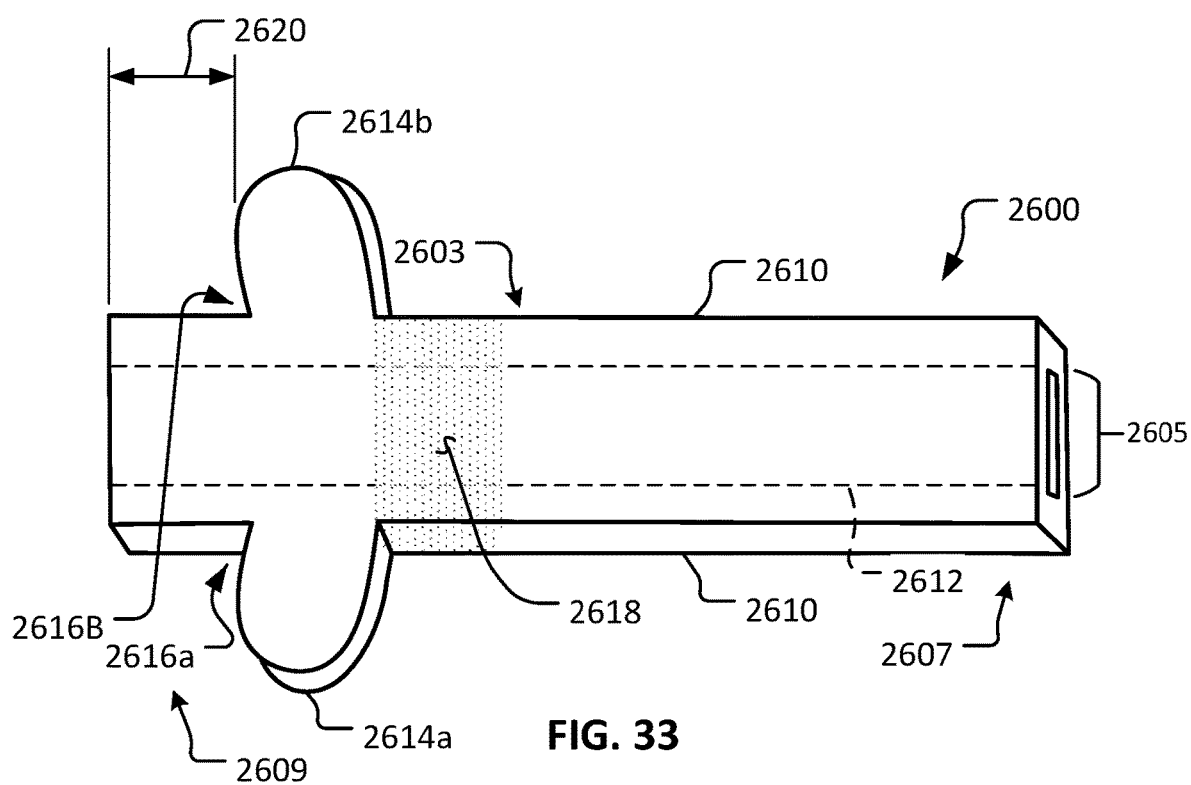
FIG. 33 is a perspective view of another example device for treating glaucoma in accordance with some embodiments.

Referring to FIG. 33, another example device 2600 in accordance with some embodiments provided herein is illustrated. Device 2600 includes a body 2603 that defines a lumen 2605. Body 2603 includes a first end 2607 and a second end 2609. Body 2603 has an external surface 2610, and a lumenal surface 2612.

Device 2600 can be constructed using any of the materials and techniques as described herein in reference to device 1. Also, device 2600 can be configured and used in any of the manners described herein in reference to device 1.

In the depicted embodiment, device 2600 is generally configured in the arrangement as device 2500 of FIG. 32. Device 2600 differs from device 2500 in that second end 2609 is extended beyond flange portions 2614a and 2614b by a distance 2620. In some embodiments, distance 2620 is about 300 µm. In some embodiments, distance 2620 is in a range from about 200 µm to about 400 µm, or from about 100 µm to about 500 µm, or from about 0 µm to about 600 µm.

Figure 34:
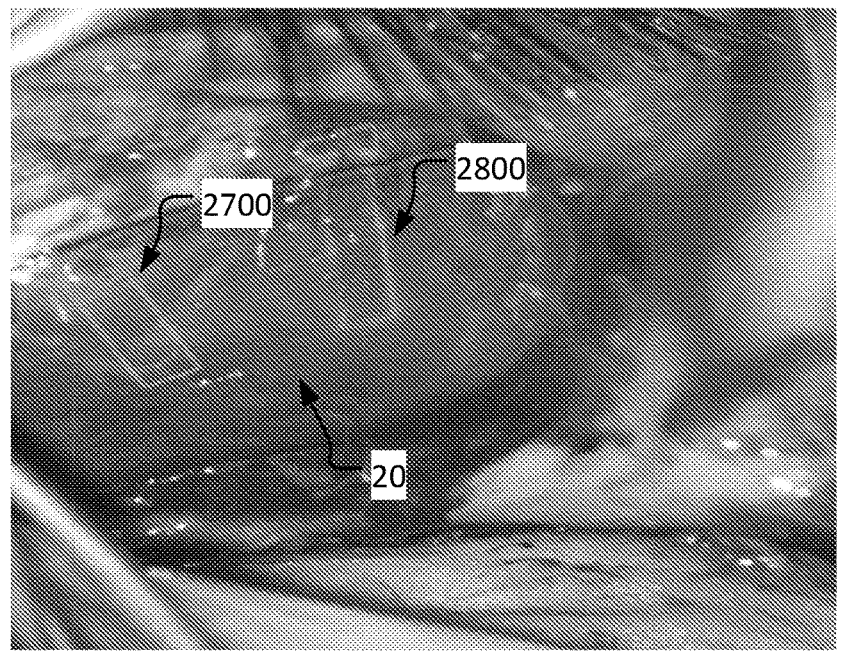
FIG. 34 is a photograph of an example eye shortly after receiving an implantation of two devices in accordance with some embodiments.

Referring to FIG. 34, example devices 2700 and 2800 can be implanted in an eye 20 that is afflicted with glaucoma.

A second method for installing the devices provided herein is as follows. Sometime before installation, the eye is irrigated with 1-5% Betadine solution, and topical antibiotic and non-steroidal anti-inflammatory drops (NSAID) are applied to the operative eye. These can be continued for about one week postoperatively four times a day. The NSAID can help stabilize the blood-aqueous barrier. All embodiments of the device illustrated herein may be inserted under topical anesthesia, possibly supplemented subconjunctivally.

This insertion procedure can be conducted without excising conjunctiva at the site of the anticipated insertion. Approximately 1-2 mm posterior to the limbus, a diamond blade can be used to make a stab incision into the anterior chamber, while held roughly parallel to the iris. The blade can be of a size predetermined to make an opening into the anterior chamber sized appropriately for the introduction of the device. This stab incision can be made gently, but relatively quickly, assiduously avoiding any and all intraocular structures.

The device is next picked up and can be held with a non-toothed forceps. The lips of the stab incision wound may be gaped with a fine, toothed forceps. The distal end (which may or may not be a pointed/beveled tip) of the tube element would then be gently pushed through the scleral tract of the stab incision and into the anterior chamber, with the device lying above and parallel to the iris, with the bevel up (i.e., anteriorly). The lateral flanges in the embodiments so configured provide for a definite endpoint to the depth of insertion. For embodiments of the device having a beveled first end, the bevel is oriented anteriorly to minimize the potential for blockage of the lumenal opening by the iris. The scleral barb(s) or other outer surface features (if included) can stabilize the device until the biointegration with the sclera is complete. This biointegration is a function of its porous cellular ingrowth surface, possibly enhanced by adsorbed growth factors and/or grafted extracellular matrix proteins. In some implementations, one or more sutures may be added using the device's suture attachment features to stabilize the device prior to biointegration. For example, a 10-0 nylon suture on a broad spatula needle may be used to suture the device the sclera, providing additional stability to the device until the biointegration is complete. This suture may then be easily removed at a later time if needed. An alternative insertion technique can include having the device pre-loaded into an insertion holder or cartridge, to limit the needed handling of the device by the surgeon. A properly sized sharp blade could be at the leading edge of the inserter, such blade acting also as a guide for implanting the device. Alternatively, the paracentesis can be made with a separate blade, followed by controlled insertion with an inserter.

After insertion of the device, an ocular shield can be placed over the eye. The implanted device can bio-integrate with the sclera, thereby reducing the risks of infections such as tunnel infection.

Figure 35:
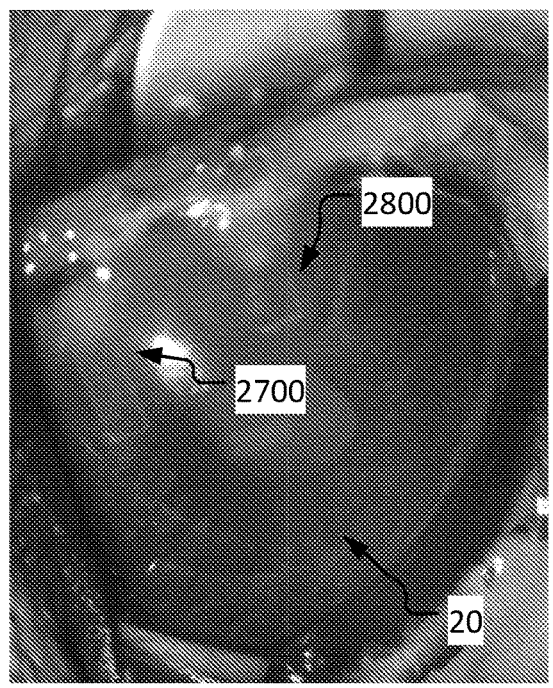
FIG. 35 is a photograph of the eye of FIG. 34 two weeks after the implantation.

Referring to FIG. 35, eye 20 is shown after devices 2700 and 2800 have been implanted for a period of approximately two weeks. The end portions of devices 2700 and 2800 have not been overgrown with conjunctival tissue. Hence, the lumens of devices 2700 and 2800 are patent and can function to reduce IOP, thereby treating glaucoma in a safe and effective manner.

Figure 36:
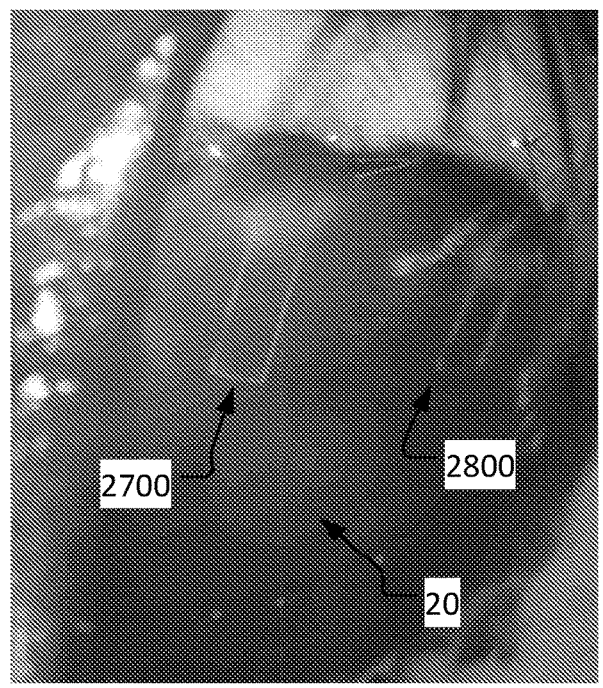
FIG. 36 is a photograph of the eye of FIG. 34 one month after the implantation.

Referring to FIG. 36, eye 20 is shown after devices 2700 and 2800 have been implanted for a period of approximately one month. The end portions of devices 2700 and 2800 still have not been overgrown with conjunctival tissue. Hence, the lumens of devices 2700 and 2800 are patent and can function to reduce IOP, thereby treating glaucoma in a safe and effective manner. In addition, the photo shows that the prior irritation (redness) of the tissue has subsided. Hence, devices 2700 and 2800 have been successfully integrated by the patient in this example.

Prevention of conjunctival tissue overgrowth to sustain patency of the device's lumen has been found to be effected by a number of various design factors such as, but not limited to, material selection, coatings, physical distance and geometry of the projection of the device from the surface of the eye, and the angle of the projecting end relative to the eye. For example, from animal experimentation, the relationships between time and projection distance (distance from the eye's surface to the end of the device) shown in Table 1 below have been observed.

TABLE 1

Amount of Conjunctival Overgrowth

| Projection Distance | 1 Week after Implantation | 2 Weeks after Implantation | 1 Month after Implantation | 2 Months after Implantation |
|---|---|---|---|---|
| 200 μm | none | partial | full | full |
| 800 μm | none | none | none | none |

Referring to FIGS. 37 and 38, another example device for treating glaucoma in accordance with the techniques provided herein is a two-piece device 2900. Two-piece device 2900 includes a collar 2910 and a cartridge 2940. Collar 2910 is configured to slidably receive cartridge 2940, such that collar 2910 and cartridge 2940 are releasably coupleable.

Figure 39:
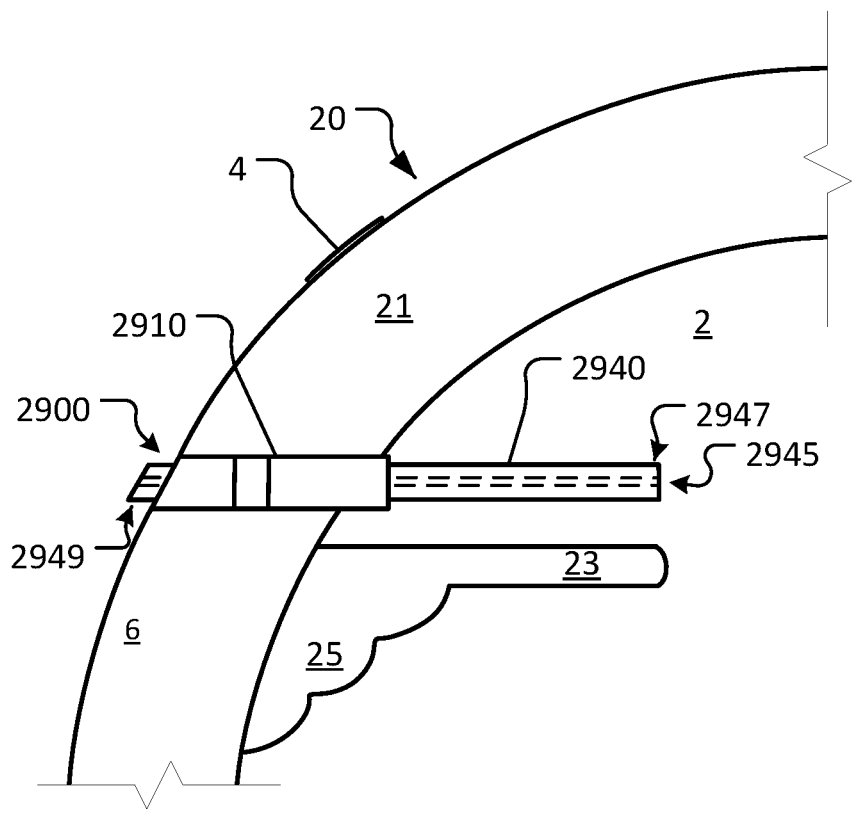
FIG. 39 is a sagittal cross-sectional schematic diagram of an eye with the device of FIG. 37 implanted in the eye.

During normal use, collar 2910 and cartridge 2940 are coupled together (as shown in FIG. 38). In that coupled arrangement, two-piece device 2900 can be implanted in a sclera of an afflicted eye to allow aqueous humor to flow from the anterior chamber of the afflicted eye through two-piece device 2900, and into the tear film (as shown in FIG. 39). This outflow of aqueous humor into the tear film can treat glaucoma by reducing the intraocular pressure of the afflicted eye, in addition to providing moisture and lubrication to the surface of the eye. Such functionality is consistent with that of other device embodiments described herein.

Along with the ability to reduce intraocular pressure, two-piece device 2900 provides added functional advantages related to the fact that collar 2910 and cartridge 2940 are releasably coupleable. For example, as described further herein, while collar 2910 remains implanted in the sclera of an afflicted eye, a used cartridge 2940 can be removed from engagement with the implanted collar 2910, and a new cartridge 2940 can be reinstalled into the implanted collar 2910. In some cases, such a procedure for installing a new cartridge 2940 is not as extensive as would be the procedure for installing an entire new single piece device. Hence, two-piece device 2900 can in some cases provide functional advantages related to the fact that collar 2910 and cartridge 2940 are releasably coupleable.

Collar 2910 and cartridge 2940 can be constructed using any of the materials and techniques as described herein in reference to device 1 and other devices provided herein. In addition, in some embodiments, collar 2910 and/or cartridge 2940, or portions thereof, are made of silicone. In some embodiments, collar 2910 and/or cartridge 2940, or portions thereof, are made of PET. Two-piece device 2900 can be configured and used in any of the manners described herein in reference to device 1. In some cases, the inner and/or outer surfaces of the two-piece device 2900 can be coated with materials such as polymer coatings or biologically active molecules, to promote surface biocompatibility and/or immobilization of the implanted device.

Collar 2910 includes a body 2912. In the depicted embodiment, body 2912 includes barbs 2912a and 2912b. One or more portions of body 2912 can be configured for enhanced friction with eye tissue (e.g., the cornea or sclera). Advantageous mechanical stability and/or migration resistance of the device two-piece 2900 (and the other devices provided herein) in relation to the eye can be facilitated by such portions. For example, in the depicted embodiment, one or more lateral barbs 2912a and 2912b are included on opposing surfaces of body 2912. In the depicted embodiment, lateral barbs 2912a and 2912b are triangular protrusions with sharp tips. Other types of shapes may be used for lateral barbs 2912a and 2912b. In some embodiments, lateral barbs 2912a and 2912b are configured to be atraumatic (e.g., truncated tips, radiused tips, and the like). In some embodiments, multiple barbs are used on one or more particular surfaces of body 2912. In some embodiments, no such lateral barbs 2912a and 2912b are included. The barbs 2912a and 2912b may be formed as part of body 2912 during manufacture, or may be fused or bonded to body 2912 using any appropriate technique.

In the depicted embodiment, a surface portion 2918 of body 2912 includes an enhanced texture (roughness) in comparison to other surface portions of body 2912. In the depicted embodiment, surface portion 2918 is a cross-hatched surface. In some embodiments, other types of texturing configurations can be alternatively or additionally included. For example, such texturing configurations can include, but are not limited to, stippling, knurling, inclusion of one or more barbs, and the like, and combinations thereof. In some embodiments, the surface portion 2918 is created by techniques such as, but not limited to, laser machining, chemical etching, 3D printing, photo etching, and the like. Such texturing can be located on all external surfaces of body 2912 in some embodiments. In specific embodiments, texturing may be located on some external surfaces of body 2912, but not on others. In some embodiments, no such texturing is included on any external surfaces of body 2912.

Body 2912 defines a lumen 2914. Lumen 2914 can extend entirely through body 2912 from a proximal end to a distal end of body 2912. In some embodiments, lumen 2914 is sized for press-fit coupling with cartridge 2940. That is, in some embodiments a dimensional interference between the sizes of lumen 2914 and cartridge 2940 may facilitate a mechanical coupling therebetween. Alternatively, or additionally, in some embodiments other mechanical coupling techniques between body 2914 and cartridge 2940 can be used. Such techniques can include, but are not limited to, use of adhesives, snap-fitting, use of welding techniques, threading, clamping, and the like, and combinations thereof.

PEG can be used to define lumen 2914, in some embodiments. The use of PEG for the surfaces of lumen 2914 can be advantageous because PEG resists bacterial, protein, and cell adherence. In some embodiments, low molecular weight PEG can be used. In some cases, the PEG is photo-polymerized. In some cases, the PEG is not photo-polymerized.

In order to facilitate a desired coupling arrangement between cartridge 2940 and lumen 2914, in some embodiments the outer dimensions of cartridge 2940 are inconsistent along the longitudinal length of cartridge 2940. For example, in some embodiments a distal portion of cartridge 2940 has smaller outer dimensions than a proximal portion of cartridge 2940. That way, when cartridge 2940 is inserted into lumen 2914, the distal portion of cartridge 2940 will slide through lumen 2914, while the proximal portion of cartridge 2940 will become coupled with lumen 2914 due to a dimensional interference therebetween.

Cartridge 2940 includes a body 2943 that defines a lumen 2945. Body 2943 includes a first end 2947 and a second end 2949. Body 2943 has an external surface 2210, and a lumenal surface 2212. Device 2200 also includes a bolster portion 2204. Bolster portion 2204 can be mated with body 2203. In some cases, second end 2209 of body 2203 can be coupled with receptacle 2218 of bolster portion 2204.

In the depicted embodiment, lumen 2945 includes a longitudinal rib 2953. While in the depicted embodiment, rib 2953 extends continuously from first end 2947 to second end 2949, in some embodiments, rib 2953 may be made of multiple individually shorter segments and/or other arrangements. It should be understood that lumen 2945 may be configured with any of the lumenal constructs provided herein (e.g., FIGS. 15-26, and others), and combinations thereof.

While in the depicted embodiment, the cross-sectional shapes of collar 2910 and cartridge 2940 are rectangular, in some embodiments, other cross-sectional shapes are used. Such cross-sectional shapes can include, but are not limited to, circles, ovals, squares, parallelograms, and the like.

In the depicted embodiment, first end 2947 is not beveled. Rather, first end 2947 is generally orthogonal in relation to the longitudinal external surfaces of body 2943. Second end 2949 of the depicted embodiment is beveled in relation to the longitudinal external surfaces of body 2943. It should be understood that, in some embodiments of two-piece device 2900 and the other devices provided herein, both ends 2947 and 2949 may be beveled, both ends 2947 and 2949 may be orthogonal, or either one of ends 2947 and 2949 may be beveled while the other one of ends 2947 and 2949 is orthogonal.

In the depicted embodiment, second end 2949 extends beyond collar 2910 (in the coupled arrangement of FIG. 38). For example, in some embodiments second end 2949 extends beyond collar 2910 by about 200 µm. In some embodiments, second end 2949 extends beyond collar 2910 by a distance in a range from about 50 µm to about 1000 µm, or from about 50 µm to about 200 µm, or from about 100 µm to about 300 µm, or from about 200 µm to about 400 µm, or from about 300 µm to about 500 µm, or from about 400 µm to about 600 µm, or from about 500 µm to about 700 µm, or from about 600 µm to about 800 µm, or from about 700 µm to about 900 µm, or from about 800 µm to about 1,000 µm. In some embodiments, while in the coupled arrangement, second end 2949 is flush or slightly recessed in relation to collar 2910.

In some embodiments, one or more suture attachment features are optionally included on two-piece device 2900 (and the other devices provided herein). For example, in some embodiments suture attachment features may be included on collar 2910. The suture attachment features can be holes, slots, flanges, and the like, and combinations thereof in the depicted embodiment.

Referring to FIG. 39, two-piece device 2900 is shown implanted in an afflicted eye 20 for the purpose of treating glaucoma of afflicted eye 20. The depicted anatomical features of eye 20 include an anterior chamber 2, a sclera 6, a tear film 4, an iris 23, a ciliary body 25, and a cornea 21. Two-piece device 2900 includes collar 2910 and cartridge 2940. Cartridge 2940 includes first end 2947 and second end 2949.

As depicted, two-piece device 2900 is configured to be surgically implanted in sclera 6 of eye 20. Two-piece device 2900 has a length sufficient to provide fluid communication between anterior chamber 2 and tear film 4 of eye 20 when two-piece device 2900 is implanted in sclera 6. As described further herein, in some embodiments, lumen 2945 can be sized and configured to provide an appropriate outflow resistance to modulate aqueous humor flowing through lumen 2945, without an element that provides additional flow resistance (e.g., a filter or a porous element). In doing so, lumen 2945 functions to maintain a desired IOP to treat a glaucoma-afflicted eye 20, while also providing moisture and lubrication to the surface of eye 20 and tear film 4. In other words, aqueous humor is shunted directly to tear film 4. No conjunctival bleb is formed. Additionally, no EVP is created that could raise nocturnal IOP. Rather, EVP is unaffected. In some cases, lumen 2945 includes a filter or a porous element.

In some cases, collar 2910 can be implanted so that the proximal end of collar 2910 is generally flush with the outer surface of eye 20. Collar 2910 can be configured with a length such that when generally flush with the outer surface of eye 20, the distal end of collar 2910 extends beyond sclera 6, just into anterior chamber 2.

In some cases, to provide fluid communication between anterior chamber 2 and tear film 4 (via lumen 2945), two-piece device 2900 has a total length of about 2.5 mm. In some embodiments, two-piece device 2900 has a total length of between about 2.5 mm and about 5.0 mm, or between about 3.5 mm and about 6.0 mm. The length of at least about 2.5 mm will reduce the possibility of blockage of the lumenal opening in anterior chamber 2 by iris 23. The length of two-piece device 2900 within the scleral tract would preferably be greater than the scleral thickness, because insertion would not be perpendicular to sclera 6 (but more tangential) to be parallel to iris 23.

As described in reference to FIGS. 37 and 38, two-piece device 2900 is configured such that cartridge 2940 can be removed from the collar 2910 while collar 2910 remains implanted in sclera 6. Thereafter, a new cartridge 2940 can be readily installed in collar 2910. Such a feature can be advantageous in various circumstances. In one example circumstance, over a period of time lumen 2945 of a used cartridge 2940 may become partially or fully occluded by biomaterials, for example. Therefore, it may become desirable or necessary to remove used cartridge 2940, and to install a new cartridge 2940. In such a case, a clinician can remove used cartridge 2940 (while leaving collar 2910 in its implanted position) and then install a new cartridge 2940 into a coupled arrangement with collar 2910.

In another example circumstance, two-piece device 2900 is configured to be adaptable to a patient's needs over time by facilitating the use of cartridges 2940 of differing flow resistances in accordance with the patient's needs. For example, physicians can prescribe different resistance levels if the patient needs more or less AH flow to treat the patient's glaucoma. When a cartridge 2940 with a different resistance level is needed by the patient, the old cartridge 2940 can be removed and the new cartridge 2940 can be installed, using the advantageous techniques (while leaving collar 2910 in its implanted position) accommodated by two-piece device 2900.

Figure 41:
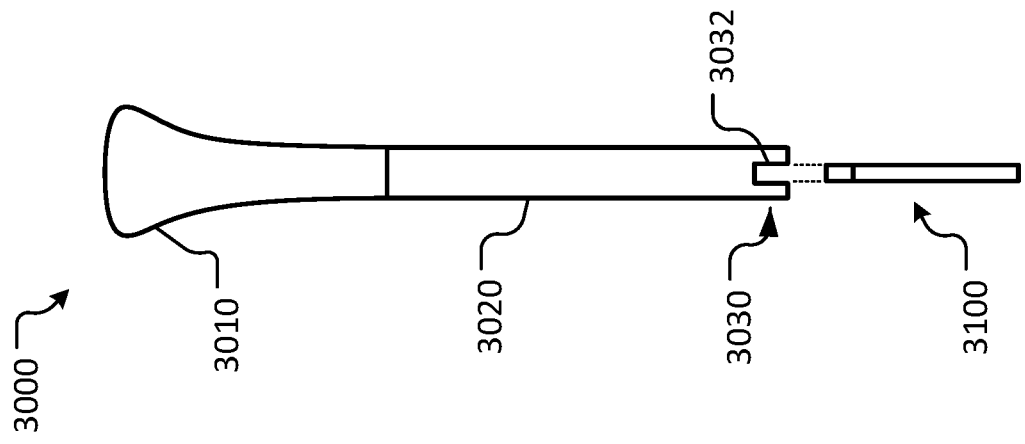
FIG. 41 is an exploded side view of the example deployment tool and the device for treating glaucoma of FIG. 40.
Figure 40:
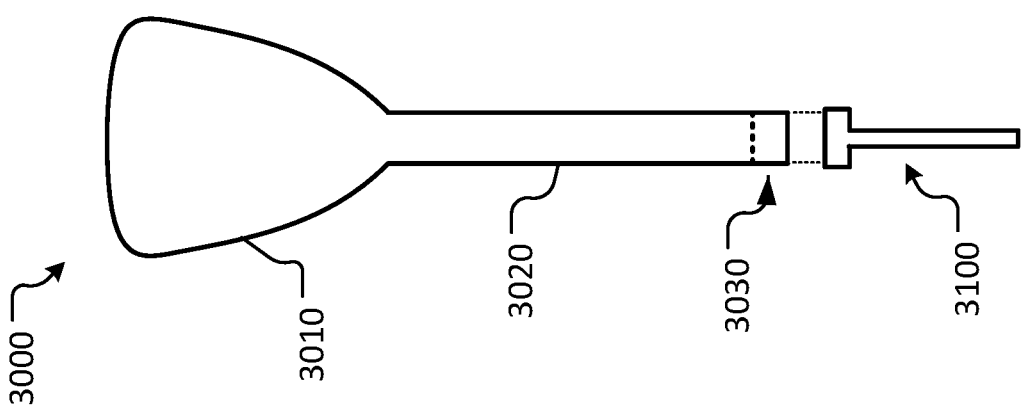
FIG. 40 is an exploded plan view of an example deployment tool and a device for treating glaucoma.

Referring to FIGS. 40 and 41, in some cases a deployment tool 3000 can be used to assist in the implantation of the glaucoma treatment devices provided herein (such as the depicted example device 3100). The use of deployment tool 3000 can be advantageous because the minute size of glaucoma treatment device 3100 can make glaucoma treatment device 3100 otherwise challenging for a clinician to handle and manipulate as needed during the implantation process.

Deployment tool 3000 includes a grasping portion 3010, a shaft 3020, and a distal end 3030 that is configured to releasably engage with device 3100. In the depicted embodiment, distal end 3030 includes a slot 3032 that is configured to releasably engage with a proximal end of device 3100. For example, in some embodiments a light interference fit can be provided between slot 3032 and proximal end of device 3100. In some embodiments, other releasable engagement techniques between distal end 3030 and device 3100 can be used. For example, in some embodiments distal end 3030 can include retractable tabs that a clinician can retract after device 3100 has been implanted in the eye of a patient. Other releasable engagement techniques are also contemplated.

In some cases, an end user clinician may receive deployment tool 3000 and device 3100 in a coupled arrangement, in a sterile package. To perform the implant procedure, the clinician would remove the coupled combination of deployment tool 300 and device 3100 from the sterile package, and use deployment tool to implant device 3100 in accordance with the implant techniques described herein. When device 3100 is implanted in the patient's eye as desired, the clinician can uncouple deployment tool 3000 from implanted device 3100.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A device for treating glaucoma in an eye, the device comprising:
    a body defining a lumen and having first and second ends and external and lumenal surfaces, said body having a length sufficient to provide fluid communication between an anterior chamber and a tear film of the eye through said lumen when said device is implanted in the eye such that: (i) the first end is in the anterior chamber, (ii) the second end is exterior to the eye, and (iii) a portion of the external surface of the body is in contract with a sclera of the eye,
    wherein the lumen is circular and open from the first end to the second end and configured to maintain a desired intraocular pressure without having a porous element inside the lumen,
    wherein the portion of the external surface of the body that is in contact with the sclera of the eye while the device is implanted in the eye is chemically etched to provide increased friction with the sclera and includes two pairs of barbs extending in opposite lateral directions from the body,
    wherein a portion of the body including the second end is laterally flared and includes a surface shaped to follow an outer contour of the eye, and
    wherein the first end is beveled.

2. The device of claim 1, wherein the body includes one or more ribs that extend longitudinally through at least a portion of the lumen, and wherein the one or more ribs define open channels for aqueous humor outflow.

3. The device of claim 1, wherein the lumenal surface of the device comprises a hydrophilic material.

4. The device of claim 3, wherein the hydrophilic material comprises polyethylene glycol.

5. The device of claim 1, wherein the external surface of the device is coated with a hetero-bifunctional crosslinker.

6. The device of claim 5, wherein the hetero-bifunctional crosslinker is 5-azido-2-nitrobenzoic acid N-hydroxysuccinimide.

7. The device of claim 1, further comprising a bolster portion configured to couple with the body, wherein the bolster portion is configured to stabilize the body in relation to the eye when said device is implanted in the eye.

8. The device of claim 1, wherein the laterally flared portion of the body including the second end is laterally wider than the two pairs of barbs.

9. The device of claim 1, wherein the second end is radiused.

10. A method for treating an eye, the method comprising:
    implanting a device in the eye, wherein the device comprises:
        a body defining a lumen and having first and second ends and external and lumenal surfaces, wherein the lumen is circular and open from the first end to the second end and configured to maintain a desired intraocular pressure without having a porous element inside the lumen, wherein a portion of the external surface of the body is chemically etched to provide increased friction with a sclera of the eye and includes two pairs of barbs extending in opposite lateral directions that engage the sclera to provide migration resistance,
    wherein, while the device is implanted in the eye: (i) the first end is in an anterior chamber of the eye, (ii) the second end is exterior to the eye, (iii) the portion of the external surface of the body is in contract with the sclera, and (iv) aqueous humor flows from the anterior chamber of the eye to a tear film of the eye through the lumen.

11. The method of claim 10, wherein, after implanting the device, the second end protrudes from the eye by a distance in the range from about 50 μm to about 1000 μm.

12. The method of claim 11, wherein a portion of the body including the second end is laterally extended and a surface of the laterally extended portion is in contact with the eye and follows a contour of the eye while the device is implanted in the eye.

13. The method of claim 10, wherein the aqueous humor flowing from the anterior chamber to the tear film of the eye increases moisture and lubrication of a surface of the eye.

14. The method of claim 10, wherein the first end is beveled, and wherein implanting the device in the eye includes making an incision through the sclera and inserting the beveled first end through the incision.

* * * * *